(12) United States Patent
Herrick, II

(10) Patent No.: US 7,404,825 B2
(45) Date of Patent: Jul. 29, 2008

(54) IMPLANT CAPABLE OF FORMING A DIFFERENTIAL IMAGE IN AN EYE

(76) Inventor: Robert S. Herrick, II, 6809 Gilbraltler, Anacortes, WA (US) 98221

( * ) Notice: Subject to any disclaimer, the term of this patent is extended or adjusted under 35 U.S.C. 154(b) by 228 days.

(21) Appl. No.: 10/164,060

(22) Filed: Jun. 5, 2002

(65) Prior Publication Data

US 2002/0198453 A1    Dec. 26, 2002

Related U.S. Application Data

(60) Provisional application No. 60/297,560, filed on Jun. 11, 2001.

(51) Int. Cl.
*A61F 2/14* (2006.01)
(52) U.S. Cl. .................. 623/4.1; 604/294; 128/887
(58) Field of Classification Search .................. 623/4.1; 604/294; 128/887
See application file for complete search history.

(56) References Cited

U.S. PATENT DOCUMENTS

| | | | | |
|---|---|---|---|---|
| 2,154,968 | A | | 4/1939 | Alkio .................. 650/540 |
| 2,467,401 | A | * | 4/1949 | Murphey et al. ........... 623/6.64 |
| 3,618,604 | A | | 11/1971 | Ness ..................... 604/294 |
| 3,626,940 | A | | 12/1971 | Zaffaroni ................ 128/260 |
| 3,683,904 | A | | 8/1972 | Forster .................. 128/834 |
| 3,726,284 | A | | 4/1973 | Parker ................... 128/3.1 |
| 3,949,750 | A | | 4/1976 | Freeman ................. 128/260 |
| 4,142,526 | A | | 3/1979 | Zaffaroni et al. ........... 424/428 |
| 4,343,787 | A | | 8/1982 | Katz .................... 424/428 |
| 4,461,295 | A | | 7/1984 | Herrick .................. 128/303.1 |
| 4,564,518 | A | * | 1/1986 | Rosenbaum ............... 424/9.1 |
| 4,650,851 | A | | 3/1987 | Rhum et al. .............. 528/354 |
| 4,660,546 | A | | 4/1987 | Herrick .................. 128/1 R |
| 4,915,684 | A | | 4/1990 | MacKeen et al. ........... 604/8 |
| 4,959,048 | A | * | 9/1990 | Seder et al. .............. 604/9 |
| 5,037,435 | A | * | 8/1991 | Chang et al. .............. 623/6.56 |
| 5,049,142 | A | | 9/1991 | Herrick ................. 604/294 |

(Continued)

OTHER PUBLICATIONS

Merriam-Webster Online Dictionary definition for "actinic."*

(Continued)

*Primary Examiner*—Paul B Prebilic
(74) *Attorney, Agent, or Firm*—Daniel J. Meaney, Jr.

(57) ABSTRACT

An implant capable of forming a differential image in an eye is shown. The implant comprises an elongated member having a pair of spaced ends wherein one of the pair of ends includes a distal section that extends in a direction substantially parallel to the central axis. The elongated member and the distal section are formed of a dimension to be inserted into and/or passed through a punctum opening of an eye and into the canaliculus. The implant incorporates into at least one of the elongated member and the distal section an energy obstructing material responsive to the application of an energy wave, such as an energy wave in the form of sound waves vibrating at frequencies greater than 20,000 cycles per second or electromagnetic radiation, which upon everting of an eyelid of an eye and exposing the implant to an appropriate energy wave, forms a differential image pattern showing the location of the implant in the eye. Methods for treating an external eye condition due to a deficiency of tears and for locating an implant in the canaliculus of an eye using the implant capable of forming a differential image is also shown.

37 Claims, 7 Drawing Sheets

U.S. PATENT DOCUMENTS

| | | | | |
|---|---|---|---|---|
| 5,049,143 | A | | 9/1991 | Gertner et al. ............... 604/304 |
| 5,053,030 | A | | 10/1991 | Herrick ................... 604/890.1 |
| 5,163,959 | A | | 11/1992 | Herrick ........................ 623/11 |
| 5,171,270 | A | | 12/1992 | Herrick ........................ 623/11 |
| 5,283,063 | A | * | 2/1994 | Freeman .................... 424/427 |
| 5,318,513 | A | | 6/1994 | Leib et al. ....................... 604/8 |
| 5,417,651 | A | | 5/1995 | Guena et al. ................... 604/8 |
| 5,423,763 | A | * | 6/1995 | Helland et al. .............. 604/174 |
| 5,423,777 | A | | 6/1995 | Tajiri et al. .................. 604/294 |
| 5,723,005 | A | | 3/1998 | Herrick ........................ 623/4 |
| 5,830,171 | A | * | 11/1998 | Wallace ......................... 604/8 |
| 5,868,697 | A | * | 2/1999 | Richter et al. .................. 604/8 |
| 5,877,243 | A | * | 3/1999 | Sarangapani ................ 524/139 |
| 5,905,561 | A | * | 5/1999 | Lee et al. ................... 623/6.31 |
| 6,016,806 | A | * | 1/2000 | Webb .......................... 128/846 |
| 6,149,684 | A | * | 11/2000 | Herrick ...................... 623/4.1 |
| 6,290,684 | B1 | | 9/2001 | Herrick ...................... 604/294 |
| 6,306,114 | B1 | * | 10/2001 | Freeman et al. ................. 604/9 |
| 6,982,090 | B2 | * | 1/2006 | Gillespie .................... 424/427 |
| 2002/0198453 | A1 | * | 12/2002 | Herrick, II ................... 600/431 |
| 2003/0100693 | A1 | * | 5/2003 | Olson et al. ................. 526/286 |
| 2007/0135914 | A1 | * | 6/2007 | Herrick, II ................... 623/4.1 |
| 2007/0299515 | A1 | * | 12/2007 | Herrick, II ................... 623/4.1 |

OTHER PUBLICATIONS

Jones LT; Marquis MM, Vincent NJ; *Lacrimal Function* pp. 658-659; Americal Journel of Ophthalmology 73; 1972.

"The Punctum Plug: Evaluation of a New Treatment for the Dry Eye"; Jerre M. Freeman, M.D.; pp. OP-874 through OP-879; Transcripts of the American Academy of Ophthalomogy and Optometry: vol. 79, Nov.-Dec. 1975.

Article entitle *Symposium on medical and surgical diseases of the cornea*, Jose I. Barraquer, MD. et al; p. 43; in the Transactions of the New Orleans Academy of Ophthalmology; C. V. Moshby Co., 1980.

Punctal Occlusion with N-Butyl Cyanoacrylate Tissue Adhesive; James T. Patten, M.D.; pp. 24 through 26; Ophthalmic Surgery; Summer 1976, vol. 7, No. 2.

Product Brochure; Umbrella Plug A2-3802 designed by J. A. Bernard, M.D.; Two Pages.

Article entitled *Intra-Canalicular Gelatin Implants in the Treatment of Kerato-Conjunctivitis Sicca*, by Wallace S. Foulds which appeared at pp. 625-627 in the Brit. J. Ophthal., vol. 45, 1961.

Product Brochure for a Tapered Shaft Punctum Plug referred to as the Super Plug sold bu Eagle Vision Four (4) pages.

Article entitled *Blinking and the Mechanics of the Lacrimal Drainage System* by Marshall G. Doane, M.D., pp. 844 through 851, Ophthalmonogy, vol. 88, No. 8, Aug. 1981.

\* cited by examiner

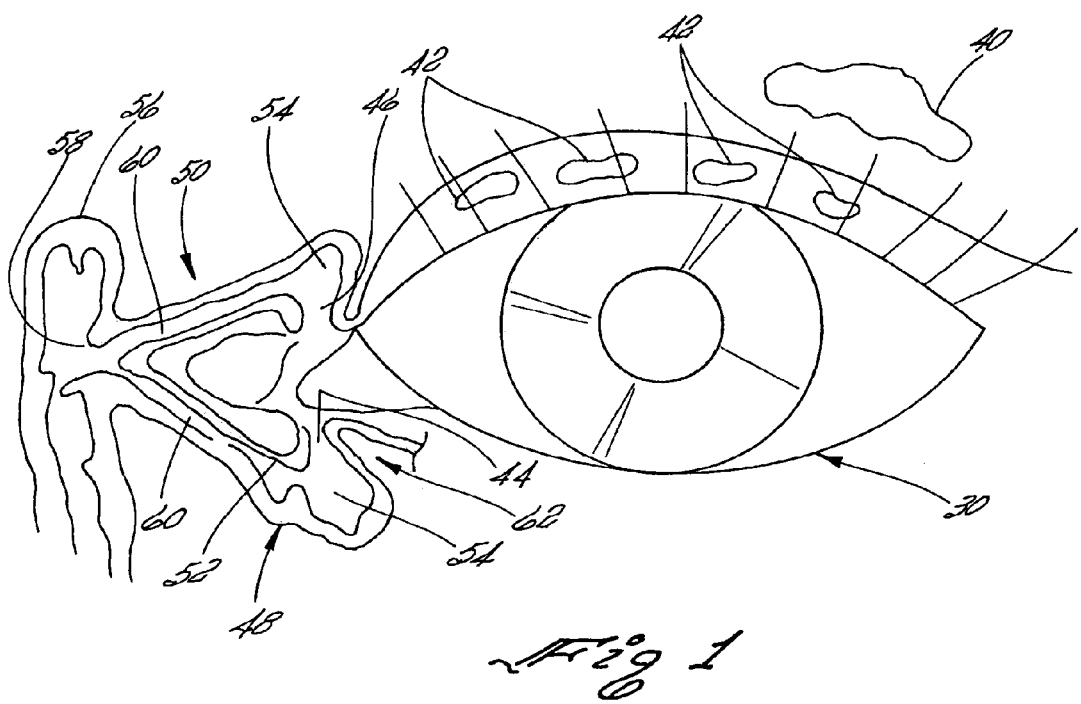
Fig 1
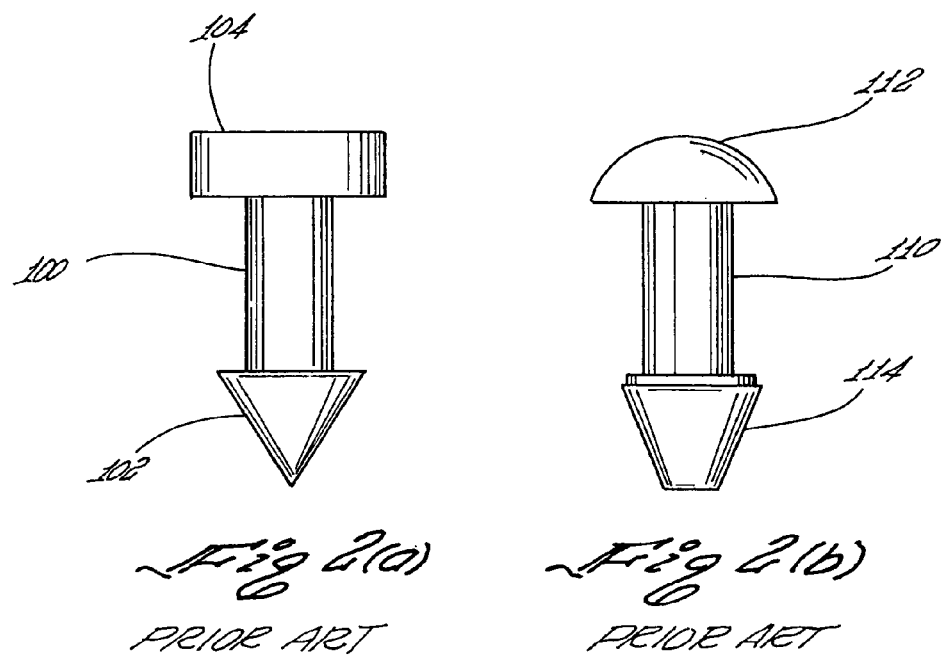
Fig 2(a)
PRIOR ART
Fig 2(b)
PRIOR ART

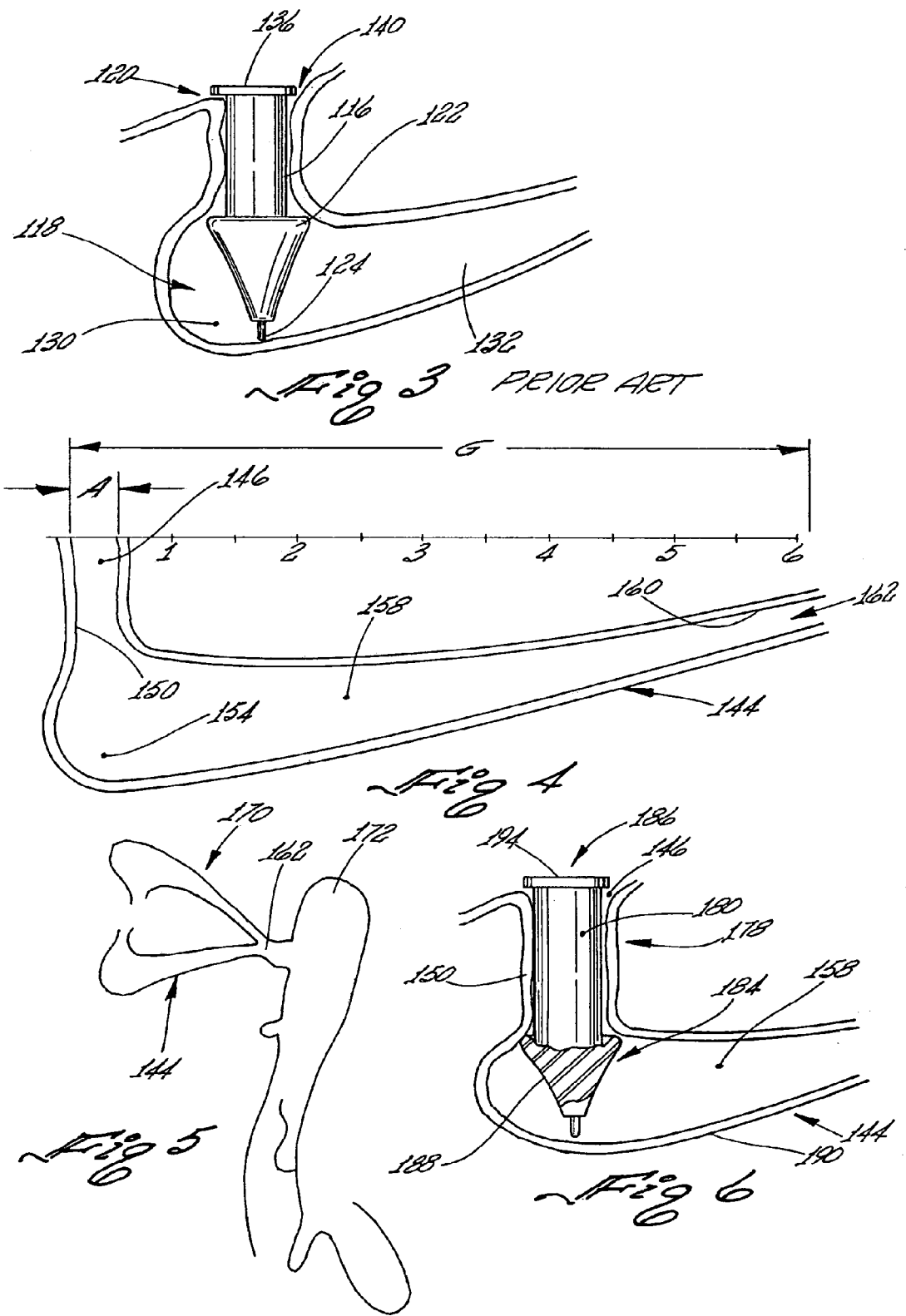

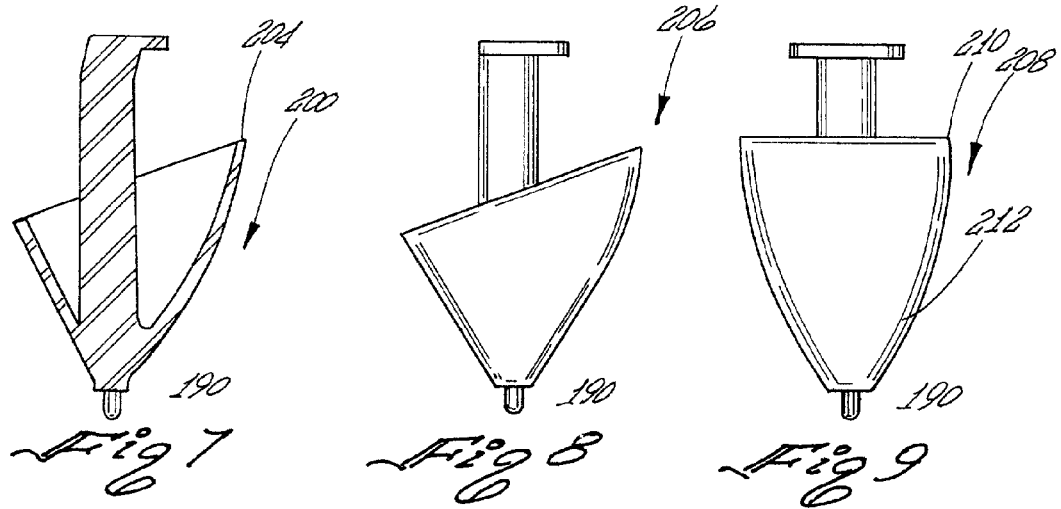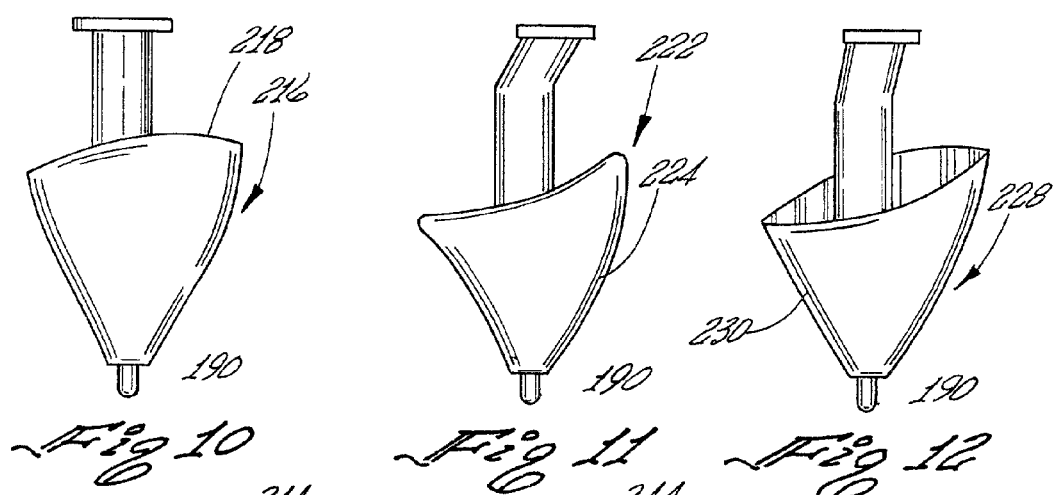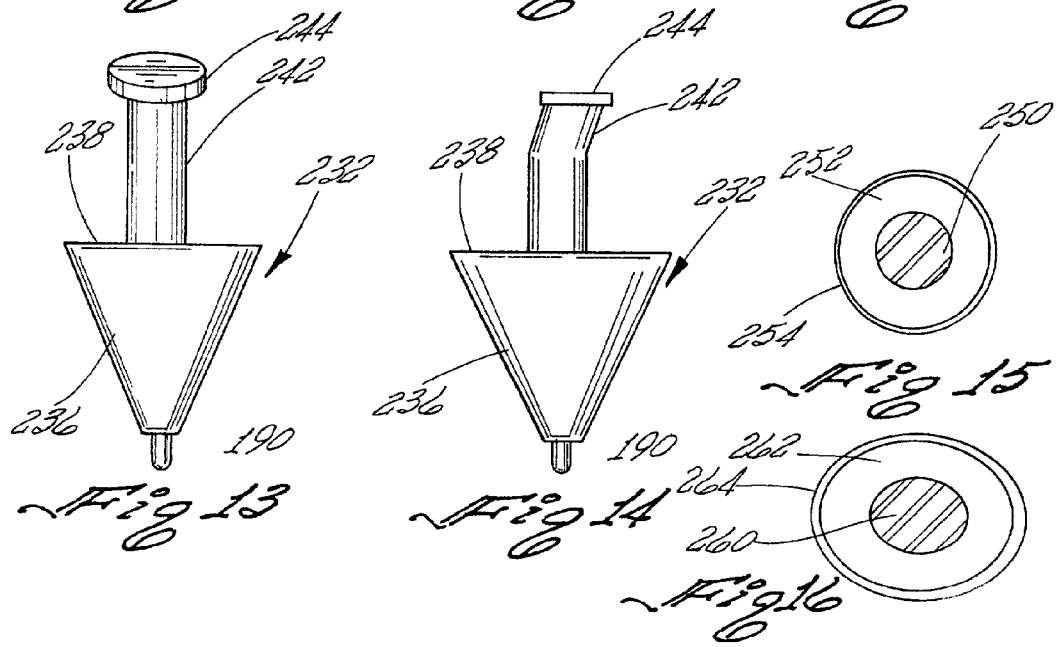

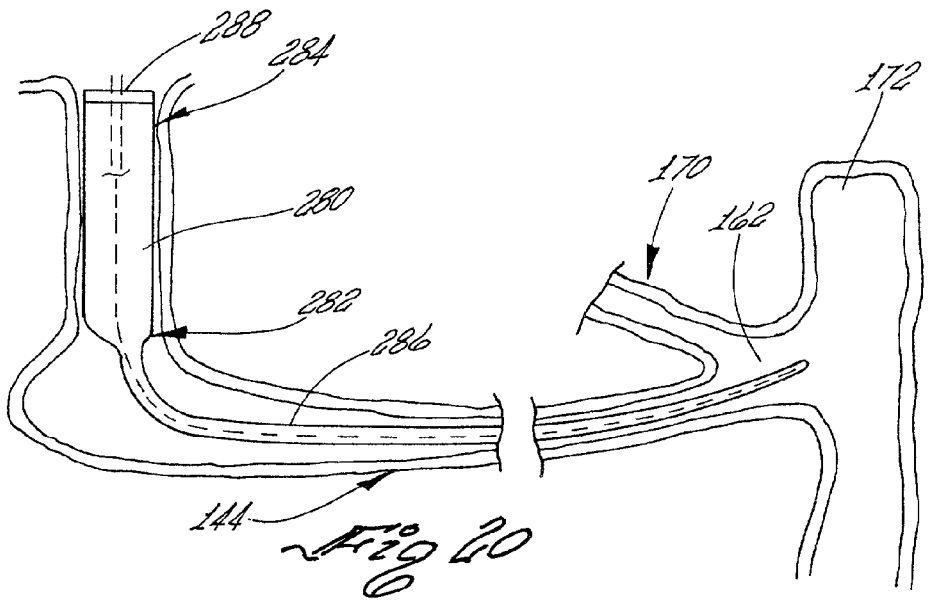
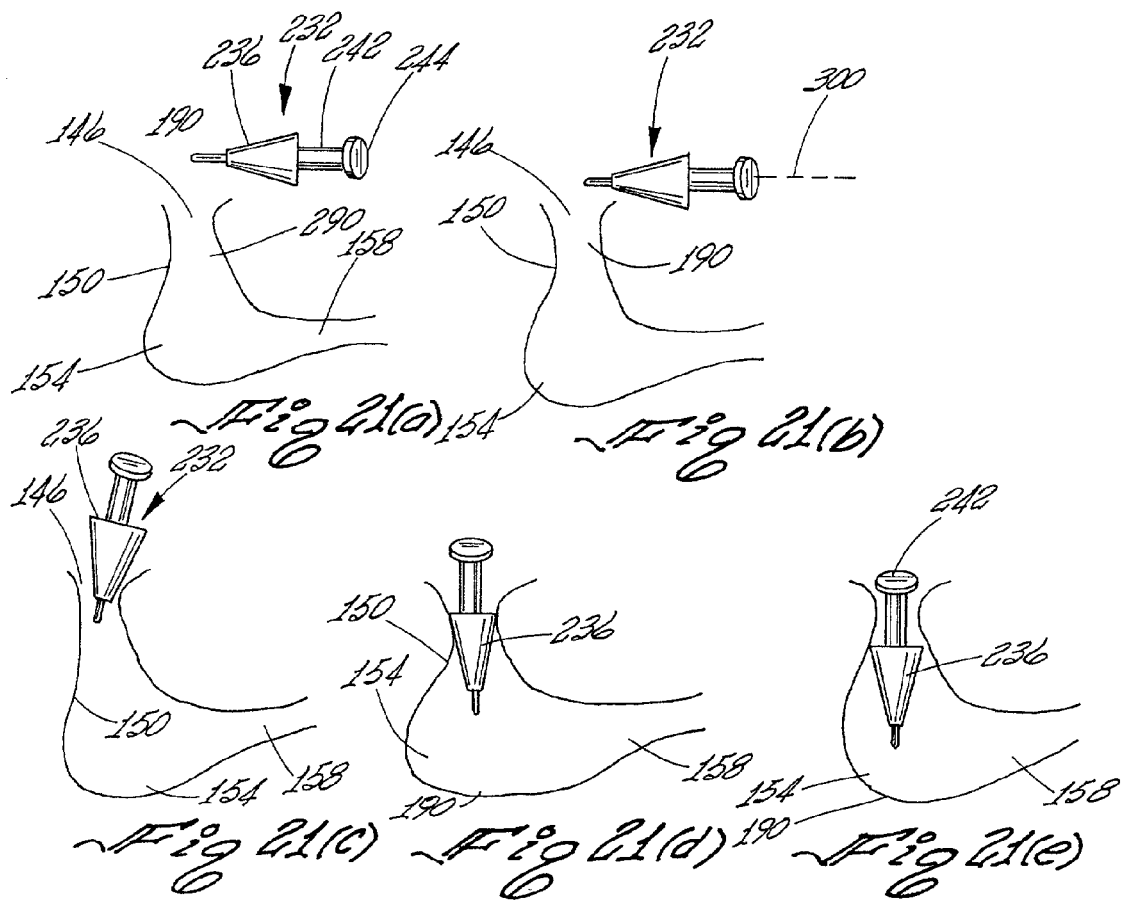

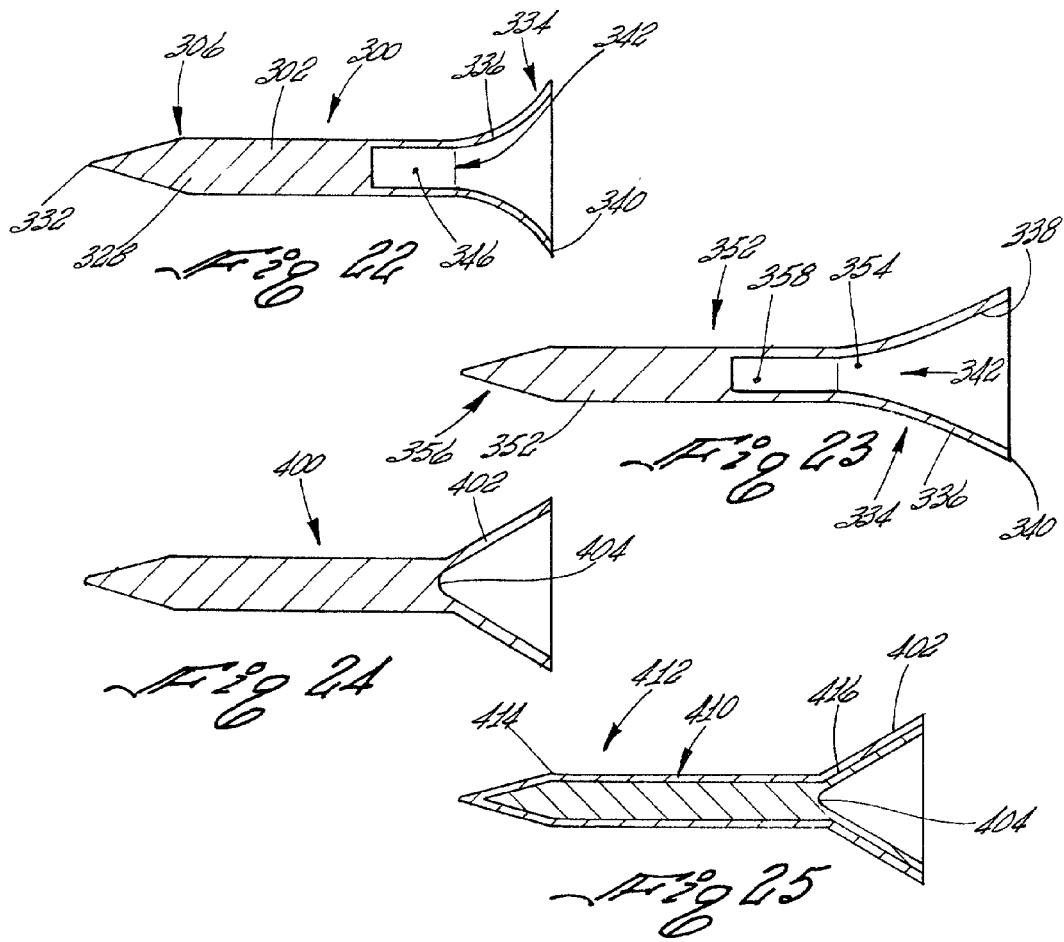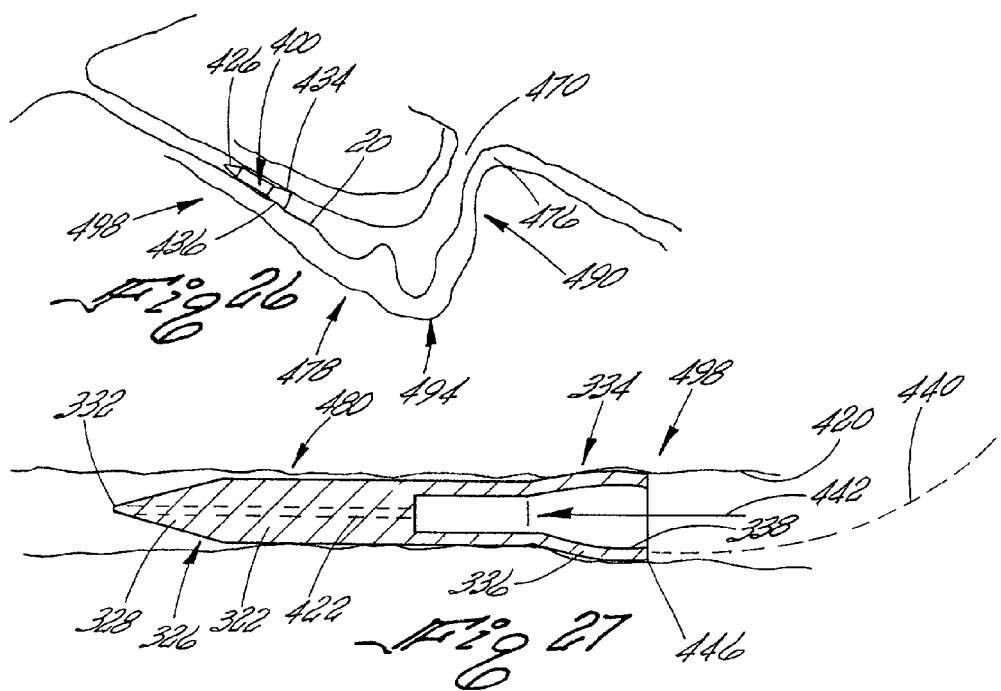

IMPLANT CAPABLE OF FORMING A DIFFERENTIAL IMAGE IN AN EYE

CROSS-REFERENCES TO RELATED APPLICATIONS

This Application claims the benefit, under Title 35, United States Code §119(e), of U.S. Provisional Patent Application Ser. No. 60/297,560 filed Jun. 11, 2001.

STATEMENT REGARDING FEDERALLY SPONSORED RESEARCH OR DEVELOPMENT

Not Applicable

REFERENCE TO A "MICROFICHE APPENDIX" (SEE 37 CFR 1.96)

Not Applicable

BACKGROUND OF THE INVENTION

1. Field of the Invention

The present invention relates to a an implant adapted to be utilized in the treatment of a human eye having a deficiency of tears and more specifically relates to an implant capable of forming a differential image in an eye wherein the implant includes an elongated member including a central axis and having at one end thereof a distal section which, in the preferred embodiment, is in the form of a collapsible expanded section.

The distal section may terminate in a distal tip which extends in a direction substantially parallel to the central axis. The elongated member including the distal section and collapsible expanded section are dimensioned to be inserted into and passed through a punctum opening of an eye into the canaliculus. In its broadest concept, an energy wave blocking material responsive to an energy wave, which may either be in be form of sound waves vibrating at frequencies greater than 20,000 cycles per second, e.g., ultrasound waves, or electromagnetic radiation is incorporated into the implant, which upon everting of an eyelid of an eye and exposing the implant to an appropriate energy wave, forms a differential image pattern showing the location of the implant in the eye.

In the preferred embodiment, a substantially opaque material responsive to electromagnetic radiation in the wavelength of visible light is incorporated into the implant which, upon everting of an eyelid of an eye and exposing the implant to electromagnetic radiation in the wavelength of visible light, forms a differential image pattern visually showing the location of the implant in the eye.

This invention also relates to a method for treating external eye conditions due to a deficiency of tears utilizing the implant having at one end thereof a distal section, preferably in the form of a collapsible flared section, terminating in a distal tip which extends in a direction substantially parallel to the central axis.

2. Description of the Prior Art

It is known in the art that certain eye problems are related to the volume of tears on the surface of the eyes. Certain of these problems include dry eyes, corneal ulcer, conjunctivitis, blepharitis, contact lens problems and many other external eye diseases.

One method for treating for a deficiency of tears is disclosed in U.S. Pat. No. 4,660,546 which discloses a method for treating external human eye conditions due to a deficiency of tears which includes the step of temporarily blockading the canaliculus of the patient and observing over a preselected period of time the response of the patient's eye to the temporary blockage and to determine if any improvement in the eye condition has been achieved in response to the occlusion.

If an improvement in eye condition is noted, an implant is placed within the canaliculus of the eye of the patient. A temporary blockading of the canaliculus is performed by placing a dissolvable, removable element, which may be in the form of a collagen material or other dissolvable material such as, for example, catgut, in the canaliculus. Unless removed shortly after insertion, the dissolvable implant is typically absorbed by the body in approximately a two-week period.

A determination is first made if the canaliculus blockage results in an improvement in the eye condition or other conditions caused by related nasal congestion warranting permanent blockage of the canaliculus, for example, the patient will respond to a partial 60% to 80% retention of constant tears.

If permanent blockage of the canaliculus is warranted, U.S. Pat. No. 4,660,546 discloses that the permanent blocking of the canaliculus is performed by utilizing a permanent implant. U.S. Pat. No. 4,660,546 discloses that the permanent implant is fabricated of a non-absorbable or non-dissolvable material and is in the form of a cylindrically shaped central body having a tapered end or an end of reduced diameter to facilitate the implantation of the implant into and for removal of the implant from the canaliculus. Both the temporary collagen implant or other dissolvable material and the permanent implant disclosed in U.S. Pat. No. 4,660,546 are in the form of a cylindrically shaped central member having a predetermined diameter which may terminate at one end in a tapered end and which reduces in diameter as it slopes away from the central member to form a tapered tip to facilitate insertion of the implant through the punctum, and into the canaliculus.

U.S. Pat. No. 4,461,295 discloses another treatment method which is a method for laser punctal occlusion. It is known in the art that punctal occlusion has been proven to be an effective way of treating patients with conditions such as sinusitis, hay fever, middle eye infection (chronic), post nasal drip, front headache and other such conditions.

The treatment method disclosed by U.S. Pat. No. 4,461,295 includes the use of a temporary suture to stitch the tear drainage canals of the eyes closed to determine if a greater tear volume on the surface of the eyes would improve certain eye problems. This diagnostic procedure has become known in the art as the Herrick Stitch Test. The Herrick Stitch Test is performed by anesthetizing the local area around the lower or upper punctum of the eye. A stitch is carefully placed to occlude the punctum by an eye surgeon utilizing magnification of the eye.

After a preselected period of time using the Herrick Stitch Test, the eye surgeon determines if the eye condition has improved, if so, then the eye surgeon permanently closes the punctum by using an ARGON laser. The punctum may be reopened at a later time if excess tearing is experienced. The reopening of the punctum can be performed by surgical and laser techniques, all as disclosed in U.S. Pat. No. 4,461,295.

It is also known in the art to utilize other plugs and or techniques for occluding the punctum. One plug device which is known in the art is referred to as a punctum plug which is described in an article by Jerre M. Freeman, MD, entitled "The Punctum Plug: Evaluation of a New Treatment for the Dry Eye" which appeared in the publication of the transcripts of the America Academy of Ophthalmology and Optometry, pages OP-874 through OP-879 (hereinafter referred to as the "Freeman Reference"). In addition, the same punctum plug is disclosed and described in U.S. Pat. No. 3,949,750.

The punctum plug disclosed in the Freeman Reference and in U.S. Pat. No. 3,949,750 is a plug that is adapted to be inserted into one or more of the upper and/or lower punctal openings of the eye to block or occlude the punctum. The punctum plug of Freeman is a rod-like plug formed with an oversized rigid or solid tip or barb portion that dilates and blockingly projects into the that portion of the canaliculus located adjacent the punctum opening.

The punctum plug has a smaller neck or waist portion around which the punctum sphincter ring or fibrous tissue defining the punctum opening tightens. The punctum plug has relatively large, smooth head portion that rests on top of the punctal opening and is intended to prevent the plug from passing down into the canaliculus. The smooth head portion is designed to be domed shaped to permit the head to rest in the lacrimal lake and against the conjunctiva and cornea, sometimes with irritation. The head portion functions to prevent the punctum plug from passing or migrating further into the canaliculus. The punctum plug of Freeman is subject to being inadvertently removed from the eye by the patient.

It is also known in the art to provide for a temporary closure of the punctum by heat using a light cautery around and in the punctal opening. The punctal closure procedure is disclosed in an article entitled "Diagnosis and Treatment of Keratoconjunctivitis Sicca" which appeared in a symposium on medical and surgical diseases of the cornea, transactions of the New Orleans Academy of Ophthalmology in 1980 at page 43 wherein the authors thereof were Jose I. Barraquer, MD and eight other authors (hereinafter referred to as the "Barraquer Reference").

The Barraquer Reference further discloses that other treatment methods of temporarily closing the punctum include use of gelatin plugs, cyanoacrylate adhesives and diathermy. The use of intracanalicular gelatin implants for treatment of eye conditions is described in an article entitled "INTRA-CANALICULER GELATIN IMPLANTS IN THE TREATMENT OF KERATO-CONJUNCTIVITIS SICCA" by Wallace S. Foulds which appeared in the Brit J. Ophthal (1961) in Volume 45 at pages 625 through 627, inclusive, (the "Foulds Reference"). The Foulds Reference discloses that occlusion of the lacrimal puncta can be performed by use of and insertion of a fine, water soluble gelatin rod into the punctal openings. The gelatin rod is formed from pure powdered gelatin to which a small quantity of distilled water has been added and is heated in a water bath until the gelatin dissolves and a thick gel results. By dipping a cold glass rod into the so prepared gelatin, and withdrawing the same, fine solid rods of gelatin were formed.

The so formed gelatin rods were then inserted into the canaliculus to provide a temporary blockage. As such, the gelatin rod implants, although very fragile, provide an alternate known means for temporarily blocking the canaliculus. If an improvement in eye condition is obtained, then permanent closure of the canaliculus may be warranted.

It is known in the art that a Schirmer's Tear Secretion Test can be utilized to measure gross tear secretion. If the results of the Schirmer Tear Secretion Test discloses that an insufficient portion of the tear secretion is retained on the eyes, a temporary or permanent occlusion of the canaliculus may prove helpful to improving the above described external eye conditions.

An improvement over the Freeman punctum plug, as described in U.S. Pat. No. 3,949,750, is shown in U.S. Pat. No. 4,915,684. U.S. Pat. No. 4,915,684 discloses a lacrimal fluid-modulating device composed of a generally cylindrical body portion with an enlarged cap at one inlet and a tapered peripheral enlargement at an outlet end. The tapered peripheral enlargement is solid. An axial bore extends completely through the modulating device and is fashioned with an outlet end having an internal diameter that is preferably no less than 0.12 and no greater than 0.36 mm.

A tapered shaft punctum plug for occlusion of the punctum opening having a tapered shaft and including one end that terminates in a narrow neck and a concave dome and another end that terminates in a solid pointed nose is offered for sale by Eagle Vision under the trademark SUPER PLUG.

Another punctum plug that is commercially available for occluding the punctum opening is known as an UMBRELLA PLUG. The UMBRELLA PLUG has an elongated cylindrically shaped central member having one end that is cut at an angle relative to the central axis and terminates in a flat, circular washer like cap or collarette. The UMBRELLA PLUG has at its other end a collapsible umbrella shaped bulb that collapses like the closing of an umbrella during insertion of the umbrella shaped bulb through the punctum and when the umbrella has passed through the punctum opening, it then reverts back to an open position.

U.S. Pat. No. 5,417,651 discloses a punctum plug and probe for lacrimal pathology that includes a plug having a flange, a neck and a foot portion or bulb portion. The flange is inclined at an angle of approximately 130° with respect to the symmetry axis. The foot portion is radially flexible from its resting position towards the symmetry axis. The punctum plug constitutes a head for a metallic mandrel which functions as a probe. The probe follows the path of the lacrimal duct and can be deflected to draw it out of the nasal cavity. The structure of the punctum plug is similar to the UMBRELLA PLUG described above.

U.S. Pat. No. 5,318,513 discloses a fixation stent and a method for using the stent to repair canalicular lacerations and to block fluid flow through a canalicular canal. The stent, adapted to be inserted into a punctum of an eyelid, includes a flexible tube portion having a proximal end, a distal end, an inflatable portion in fluid contact communication with the distal end, and a plug for sealing and anchoring the proximal end with a body canal. The plug includes a T-top portion with a diameter greater than the diameter of he punctum that rests at two specific locations on the margin of the eyelid, thereby anchoring the proximal end of the stent at the margin of the eyelid.

As is evidenced by the above described prior art, the two approaches used to occlude the lacrimal drainage system are to: (a) occlude the punctum opening and that portion of the canaliculus adjacent the punctum opening, e.g., Freeman U.S. Pat. No. 3,949,750, U.S. Pat. No. 4,915,684 the SUPER PUNCTUM PLUG, the UMBRELLA PLUG and the head plug to support a mandrel as shown in U.S. Pat. No. 5,417,651; and (b) occlude the canaliculus at a location other than adjacent the punctum opening, between the punctum opening and lacrimal sac, e.g., U.S. Pat. Nos. 4,660,546 and 5,049,142. However, other implants which can be used to occlude the canaliculus both adjacent the punctum opening and at other locations in the canaliculus and sometimes referred to as canalicular implants, are U.S. Pat. Nos. 5,163,959 and 5,171,270.

The use of a punctum plug as a head for a metallic mandrel which functions as a probe, e.g. U.S. Pat. No. 5,417,651 and for an anchor for a stent to repair canalicular lacerations and to block fluid flow through a canalicular canal, e.g. U.S. Pat. No. 5,318,513, basically are punctum plugs known in the art as described above.

U.S. Pat. No. 4,959,048 discloses a reversible, flexible, lacrimal duct occluder that is formed of a shaft having a low profile cap at one end and a rounded tip at the other end. The shaft has at least one, and preferably 1 through 3, conical ranges forward on the shaft between the ends. The rounded tip enters the punctum followed by the leading edge of the range(s) until the occluder bends at an acute angle relative to the axis of the shaft and enters the horizontal canalicular canal.

In practice, however, it has developed that the transition from that portion of the canaliculus adjacent the punctum opening, sometimes referred to as the vertical portion of this canaliculus, does not occur as a distinct transition point, but rather occurs through an intermediary section referred to as the ampula which anatomically appears to be an extension of that portion of the canaliculus that extends horizontally to the nasal sac.

Therefore, an implant which occludes the punctum opening and that portion of the canaliculus adjacent the punctum opening, depending on its length, can have a portion thereof located in the ampula. By occluding the lacrimal drainage system in this manner, it is not necessary that the implant physically be located in the portion of the canaliculus beyond the ampula to be effective.

On the other hand, if an implant, without a dome or collarette, is inserted into the punctum opening or the portion or section of the canaliculus adjacent the punctum opening, that implant usually migrates through the punctum opening, through the portion of the canaliculus adjacent to the punctum opening, into the ampula, and can easily migrate into that portion of the canaliculus beyond the ampula.

As the use of implants increases to treat the eye, several problems have been encountered. For example, the punctum plug, of which Freeman U.S. Pat. No. 3,949,750, U.S. Pat. No. 4,915,684, the SUPER PUNCTUM PLUG, the UMBRELLA PLUG sometimes migrate completely through the punctum opening and into the canaliculus. In certain instances, implants used to occlude the canaliculus at a location other than adjacent the punctum opening, for example, between the punctum opening and nasal sac sometimes migrate within the canaliculus. In such cases, it is desirable to be able to locate the implant within the canaliculus in order to remove the implant.

In certain patients, an implant inserted into or implanted with the canaliculus can be located and removed by massaging the canaliculus to urge the implant back out of or retrograde through the canaliculus through the punctum opening, which may require mechanical dilation of the punctum. Alternatively, the implant may be urged through the canaliculus to the nasal sac enabling expulsion of the same through the nose.

It is known in the art to use lacrimal irrigation and lacrimal probing of the canaliculus to remove an implant. Another known method for locating and removing an implant involves an invasive procedure, which is undesirable, wherein the canaliculus wall is surgically opened for visually locating the implant, for removing the located implant and then for suturing the canaliculus wall to surgically reclose the wall and adjacent tissue.

Herrick U.S. Pat. No. 5,163,959 discloses at column 13, lines 46 through 59, that a canalicular implant could include material which is responsive to actinic radiation, such as for example, X-rays, so that the eye surgeon can perform tests to determine if the canalicular implant is properly located within the horizontal section of the canaliculus. One such material that can be used is barium, in appropriate concentrations known to persons skilled in the art, so as to be responsive to actinic radiation such as X-rays. The use of such material responsive to actinic radiation is of such low enough level that it does not cause any adverse effects to the patient into which a canalicular implant containing the same is implanted. In such an application, normal X-ray procedures would be used to develop the X-ray image on film to locate the implant.

The problem of locating an implant within the canaliculus is overcome by the teachings of the present invention.

BRIEF SUMMARY OF THE INVENTION

The present invention discloses a new, novel and unique implant capable of forming a differential image in an eye. The implant comprises an elongated member having a pair of spaced ends wherein one of the pair of ends includes a distal section which extends in a direction substantially parallel to the central axis. The elongated member and the distal section are formed of a dimension to be inserted into and passed through a punctum opening of an eye into the canaliculus. An energy obstructing material responsive to the application of an energy wave is incorporated into at least one of the elongated member and the distal section which, upon everting of an eyelid of an eye and exposing the implant to an energy wave, forms a differential image pattern showing the location of said implant in the eye.

The energy obstructing material may be selected to be responsive to the application of an energy wave in the form of sound waves vibrating at frequencies greater than 20,000 cycles per second which, upon everting of an eyelid of an eye and exposing the implant to an energy wave in the form of sound waves vibrating at frequencies greater than 20,000 cycles per second, forms a differential image pattern showing the location of said implant in the eye.

The implant energy obstructing material may be selected to be responsive to the application of an energy wave in the form of electromagnetic radiation at a selected frequency which upon everting of an eyelid of an eye and exposing the implant to an energy wave in the form of electromagnetic radiation at the selected frequency forms a differential image pattern showing the location of said implant in the eye.

In the preferred embodiment of the present invention, the implant is adapted to be inserted into the punctum opening of an eye and to be transported into that part of the canaliculus adjacent the punctum opening between the punctum opening and the ampula. If the implant is of sufficient length the distal section can be transported into or through the ampula of the canaliculus to occlude the punctum opening and that portion of the canaliculus adjacent the punctum opening. The implant includes an elongated member having a first end and a spaced, opposed second end and a central member. In the preferred embodiment, the first end is slightly angularly disposed from the second end. The second end has a collapsible flared section that terminates in an outer edge or ring having dimension which is greater than the cross-sectional dimension of the central member.

The collapsible flared section has an expanded position and a collapsed position wherein the dimension of the collapsed position is approximately equal to the geometrical dimension of the punctum opening of an eye adapted to receive the same. The application of a radial force to the collapsible flared section in a direction to collapse the outer edge thereof urges the collapsible flared section from its extended position into its collapsed position. If the length of the punctum plug is selected to keep the collapsible flared section within the that portion of the canaliculus adjacent the punctum opening, the clamping force developed between the collapsible flared section and interior side walls of the canaliculus holds the punctum plug in place.

If the punctum plug has sufficient length, once the collapsible flared section passes through the punctum opening and that portion of the canaliculus adjacent the punctum opening and into the ampula, the collapsible flared section reverts back to its substantially extended position. The canalicular implant may be fabricated from a biodegradable material if it is to be used as a temporary implant, or may be formed of a non-biodegradable material if it is to be used as a permanent implant.

The known prior art implants for providing temporary and permanent occlusion of the punctum opening has certain disadvantages. One disadvantage is that a temporary implant, disclosed by the prior art, may have to be removed before it has been fully dissolved or absorbed, as the case may be. If the eye surgeon is unable to remove any part of or all of the temporary implant, the portion of the temporary implant not removed must remain in the canaliculus until it ultimately is dissolved in the body thereby terminating the occlusion of the canaliculus.

Typically, an eye surgeon will utilize the temporary implant as a means for determining if the permanent occlusion of the canaliculus will result in an improvement of eye conditions as described hereinbefore. It is possible for the temporary collagen implant, if inserted into the punctum opening or into that portion of the canaliculus adjacent to the punctum opening, for example, to migrate into that portion of the canaliculus located beyond the ampula or back out of the eye or to otherwise not remain in place. Also, the temporary implants may be too fragile to remove in a single piece during removal thereof, if required, by the eye surgeon.

In addition, the insertion and use of a permanent implant having a central body and a tapered end, which is usually formed of a non-absorbable or non-dissolvable material, can be utilized to permanently occlude either the that portion of the canaliculus located between the punctum opening and ampula. However, such a permanent implant can still migrate within the lacrimal system and into that portion of the canaliculus located beyond the ampula or out of the eye. Any migration of a permanent implant is undesirable and such an implant can be located and removed using the teachings of the present invention.

The laser treatment to obtain punctal occlusion, although quite effective, has certain disadvantages. One disadvantage is injection of a local anesthetic is required and the patient may experience some pain or discomfort for one to two days after the procedure. Also, some discharge may occur for seven to ten days. Vision may be blurred for a few days. If the patient wears contact lens, the contact lens may be uncomfortable for a few days.

The other known punctum plugs have a convex dome or collarette to act as a cap to prevent the punctum plug from migrating through the punctum opening, through that lateral portion of the canaliculus adjacent the punctum opening, into the ampula or into the medial portion of the canaliculus beyond the ampula. Such caps are generally circular and result in an edge which engages, contacts or otherwise abrades the cornea.

Therefore, one advantage of the implant of the present invention is that the punctum plug or implant, when passed in the punctum opening into the lateral portion of the canaliculus adjacent the punctum opening, will be held in place and restricted from movement by a thin elongated lip which is located on the elongated member the thin elongated lip is positioned to extend in a generally anterior direction and is urged against the edge or sphincter muscle of the punctum opening and the lid margin. The collapsible expanded section of the implant, which in the preferred embodiment is a collapsible flared section, is located with the distal section either within that portion of the canaliculus, adjacent the punctum opening, or within the ampula. If the implant is visible within the punctum opening, removal thereof is relatively easy. If the implant migrates through the punctum opening into the canaliculus, the migrated implant can be located and removed using the teachings of the present invention, usually without an invasive surgical procedure.

Another advantage of the present invention is that the implant includes a collapsible expanded section which has an outer edge which is slideably urged against the interior walls of the punctum opening during insertion and placement within that portion of the canaliculus adjacent the punctum opening to hold the implant in position while concurrently occluding the canaliculus.

Another advantage of the present invention is that the canalicular implant is relatively easy to insert without the necessity of using an injectable anesthetic and can likewise be easily removed when located.

Another advantage of the present invention is that the permanent implant, when positioned in the punctum opening and that portion of the canaliculus adjacent the punctum opening, does not cause any tissue irritation or irritation to the eye due to migration of the same out of the canaliculus and through the punctum opening into the eye, but if the implant migrates, it can be located within the canliculus.

Another advantage of the present invention is that the punctum plug or implant using the teachings of the present invention is easily removable and does not cause any discomfort, does not cause any pain to the patient or to the cornea of the eye of a patient, there is no discharge for several days, the patient's vision is not subject to blurring for several days and, if the patient wears contact lens, the contact lens will not be uncomfortable for several days.

Another advantage of the present invention is that due to the holding action between the collapsible expanded section of the medial end of the implant and the thin elongated lip which is located on the elongated member to position the tip to extend in a generally anterior direction and which is urged against the edge or sphincter muscle of the punctum opening and the lid margin, the canalicular implant cannot be easily or readily dislodged by patient activity or movement, and if the implant does become dislodged, it can be located within the canaliculus using the teachings of the present invention.

Another advantage of the present invention is that the punctum plug or implant causes no long-term discomfort to the user when the same is in place.

Another advantage of the present invention is that the punctum plug or implant is effective in blocking a drainage of tears through the punctum opening and that portion of the canaliculus adjacent the punctum opening. Thus, if only a partial blockage of drainage of tears is required, the punctum plug or implant can having a fluid metering opening extending axially therethrough.

Another advantage of the present invention is the collapsible expanded section of the punctum plug or implant can include a hollowed out central area which defines a thin walled, conical-shaped flared section.

Another advantage of the present invention is that the thin walled, conical-shaped flared section can terminate in an outer edge.

Another advantage of the present invention is that the elongated member may have a slight angular curve to urge the thin retaining lip into engagement with the edge of the punctum opening and away from or anterior from the cornea.

Another advantage of the present invention is that the collapsible flared section can be non-uniform such as being cut at a bias or having a non-circular cross-section, such as being elliptically shaped.

Another advantage of the present invention is that the collapsible flared section of the canalicular implant can include a tool-receiving opening in the central section thereof which is adapted to cooperate with an insertion tool.

Another advantage of the present invention is that the collapsible expanded section can be in the form of a convex shaped head located adjacent the distal tip and includes an annular shaped ring located on a side opposite to said distal tip.

Another advantage of the present invention is that the collapsible expanded section can be in the form of a convex shaped head located adjacent the distal tip and includes convex shaped head includes a second annular shaped outer ring located on a side opposite to said distal tip.

Another advantage of the present invention is that the cross-section diameter of the central member preferably would have a diameter of about 0.3 mm to about 1.2 mm while the outer edge of the collapsible flared section can have a diameter in the order of about 0.5 mm to about 2.2 mm.

Another advantage of the present invention is that the punctum plug or implant can be formed of a nonabsorbable or non-dissolvable material such as silicone, Polytetrafluoroethylene (e.g. Teflon) or other medically compatible or medical grade non-biodegradable material.

Another advantage of the present invention is that the punctum plug or implant could be formed of an absorbable or dissolvable material to function as a temporary implant. One such absorbable or dissolvable material that could be utilized for practicing this invention is collagen.

Another advantage of the present invention is that the length of the punctum plug can be selected to place the collapsible expanded section in that portion of the canaliculus adjacent the punctum opening or place the collapsible expanded section in the ampula.

Another advantage of the present invention is that a method for treating an external eye condition due to a deficiency of tears using the punctum plug of the present invention which can be used for treating an eye.

BRIEF DESCRIPTION OF THE DRAWINGS

The foregoing and other advantages of this invention will be apparent from the following description of the preferred embodiment of the invention when considered with the illustrations and accompanying drawings which include the following Figures:

FIG. 1 is a pictorial representation of a lacrimal system of the eye having an upper and lower canaliculi, each of which have a punctum opening, that portion of the canaliculus adjacent the punctum opening, an ampula and a that portion of the canaliculus beyond the ampula terminating in the nasal sac;

FIG. 2(a) is a pictorial representation in cross-section of a prior art Freeman punctum plug implanted in the punctum opening and in that portion of the canaliculus adjacent the punctum opening;

FIG. 2(b) is a pictorial representation in cross-section of another prior art Freeman punctum plug implanted in the punctum opening and in that portion of the canaliculus adjacent the punctum opening;

FIG. 3 is a pictorial representation of a punctum plug having a collapsible expanded section that terminates in a distal tip which is substantially co-axial with and substantially parallel to the central axis of the elongated body located within the ampula which forms part of the horizontal portion of the canaliculus and wherein the implant has an energy blocking material incorporated therein;

FIG. 4 is a diagrammatic representation of a canaliculus which extends from the punctum opening, that portion of the punctum opening adjacent the punctum opening, the ampula, that portion of the canaliculus extending beyond the ampula and the medial opening thereof into the nasal sac;

FIG. 5 is a pictorial representation of an anterior and posterior lacrimal system that communicates with an opening in the nasal sac;

FIG. 6 is a pictorial representation in cross-section of an implant used as a punctum plug incorporating the teachings of this invention implanted in the punctum opening and in that portion of the canaliculus adjacent the punctum opening with the distal section located in the ampula and wherein the implant has an energy blocking material incorporated therein;

FIG. 7 is a pictorial representation partially in cross-section of another embodiment of an implant used as a punctum plug incorporating the teachings of this invention where the collapsible extended section has a sloping outer edge and terminate in an elongated distal starting tip which extends substantially parallel to the axis of the elongated body and which is deflected at the second end thereof;

FIG. 8 is a front elevational view of yet another embodiment similar to that illustrated in FIG. 7 wherein the elongated body is substantially straight;

FIG. 9 is a left side plan view of still yet another embodiment similar to that illustrated in FIG. 7 wherein the elongated body is substantially straight and the outer edge of the collapsible expanded section is substantially planar;

FIG. 10 is a front elevational view of a punctum plug similar to that illustrated in FIG. 8 wherein the outer edge has a slight upward curve;

FIG. 11 is a left side plan view of an implant used as a punctum plug similar to that illustrated in FIG. 7 having a non-uniform shaped collapsible expanded section;

FIG. 12 is a front elevational view of an implant used as a punctum plug similar to that illustrated in FIG. 7 having a non-uniform shaped collapsible expanded section;

FIG. 13 is a front elevational view of an implant used as a punctum plug having a collapsible expanded section in the form of a collapsible flared section having a planar outer edge and a second end which is deflected at a slight angle to position the thin elongated lip anterior to the cornea of an eye using the teachings of this invention;

FIG. 14 is rotated front elevational view of the embodiment of the implant used as a punctum plug illustrated in FIG. 13 illustrating the relationship between the second end and the thin elongated lip;

FIG. 15 is a pictorial representation, in cross-section, showing an embodiment wherein the cross-section of the central member and outer edge of the collapsible flared section are both circular and utilizes the teachings of this invention;

FIG. 16 is a pictorial representation, in cross-section, showing an embodiment wherein the cross-section of the central member and outer edge of the collapsible flared section are both oval and utilizes the teachings of this invention;

FIG. 20 is a pictorial representation of an implant used as a punctum plug of the present invention using the teachings of this invention used as an anchor for a stent to repair canicular lacerations and to block fluid flow through a canalicular canal;

FIGS. 21(a), 21(b), 21(c), 21(d1) and 21(e) illustrate the various steps of inserting an implant in the form of the implant illustrated in FIG. 6 through the punctum opening and into the canaliculus;

FIG. 22 is a cross-sectional view of another implant using the teachings of this invention in the form of a canalicular implant having central opening in the center of the collapsible flared section which is adapted to cooperate with an insertion tool;

FIG. 23 is a cross-sectional view of yet another embodiment of a canalicular implant of FIG. 22 having an elongated central opening which is adapted to cooperate with an insertion tool;

FIG. 24 is a cross-sectional view of an alternate embodiment of a canalicular implant of FIG. 22 having a "VI" shaped central section which is adapted to cooperate with an insertion tool;

FIG. 25 is a cross-sectional view of the canalicular implant of FIG. 24 having the radiation blocking material coated thereon in lieu of the material being disseminated within part of or all of the implants;

FIG. 26 is a pictorial representation of the final location of a canaliculus implant using the teachings of this invention after insertion into the canaliculus;

FIG. 27 is an enlarged pictorial representation showing the collapsible flared section of the canalicular implant of FIG. 22 in its collapsed position when the same is positioned within and occludes the horizontal section of the canaliculus;

DETAILED DESCRIPTION OF THE INVENTION

Figure 17:
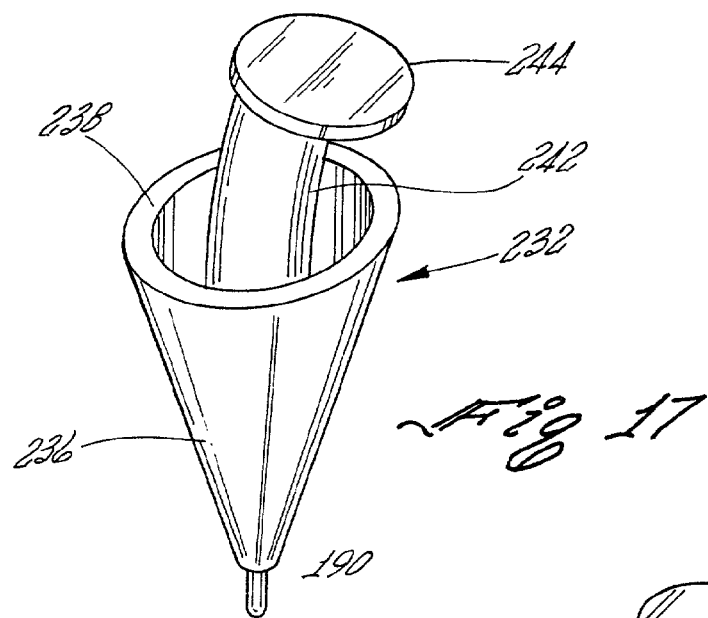
FIG. 17 is a front top and left side perspective view of the implant used as a punctum plug illustrated in FIGS. 13 and 14.

In order to better understand the teachings of the present invention, and the structure of the eye in its relationship to the present invention, the following brief description of the human eye and the associated lacrimal system illustrated in FIG. 1 and showing the paths of the tears from sources of the tears to the nasal cavity, will first be discussed.

The eye 30 includes a cornea and a pupil that is well known in the art. The source of the tears for the eye is generally classified into "crying tears" and "constant tears". The "crying tears" are produced by a large lacrimal gland 40 illustrated in the upper right hand portion of the illustration of eye 30. The "constant tears" are produced by a series of small glands 42 which are located below the large gland 40 and spaced apart above the cornea of the eye 30. The "constant tears" are the tear secretions which are to be preserved in accordance with the teachings of the present invention.

In the normal eye, approximately 400 drops (9.5 milliliters) of tear secretion are produced during the day and a lesser volume of tear secretion is produced at night during sleep. Tear secretion also protects the eye from infection since the tears contain an enzyme called Lysozyme that functions as an antibiotic. With age, the eye produces less tear secretion, about sixty percent (60%) less at age 65 than at age 18. The tears flow over the eyes and drain through the small openings called the puncta, or punctal openings or punctum openings.

There are two punctal openings in the eye, a lower punctum opening 44 and an upper punctum opening 46. The punctal openings 44 and 46 form openings into the corresponding a lower canaliculus 48 and an upper canaliculus 50, respectively. Each of the punctal openings 48 and 50 have a fibrous tissue ring or sphincter tissue, illustrated as 52, formed therearound. The fibrous tissue ring 52 is a fairly dense relatively avascular connective ring of tissue. The lower canaliculus 48 and the upper canaliculus 50 are connected to a lacrimal sac 56. The lacrimal sac 56 is connected to a nasal lacrimal duct 58. The lacrimal duct 58, in turn, extends into the nasal cavity as illustrated in FIG. 5. The tears produced by the eye travel through the punctal openings, through their associated canaliculus.

As the tears exit the lower canaliculus 48 and the upper canaliculus 50, the tear flows merge in the lacrimal duct 58 and then travel to the nasal cavity. Lower canaliculus 54 and the upper canaliculus 50, which comprise the drainage channels of the eye travel to the nasal cavity. Lower canaliculus 48 and the upper canaliculus 50, which comprise the drainage channels of the eye travel to the nasal cavity. Lower canaliculus 48 and the upper canaliculus 50, which comprise the drainage channels of the eye are connected to an ampula, shown generally as 54, which has a dimension of about 2 mm to 3 mm at its widest portion. The ampula 54 forms part of an narrows into the horizontal portion of the canaliculus, shown generally as 60.

The horizontal portion of the canaliculus of that part of the canaliculus, located between the ampula 54 and nasal sac 58, has a diameter in the order of about 0.5 mm and an overall length of about 8 mm. In practicing the present invention, the implant is inserted into and past the punctum opening. The implant is a lacrimal occluder in that the implant occludes lacrimal drainage within the lacrimal system. The implant may be used as a punctum plug or as a lacrimal implant (the lacrimal implant sometimes being also referred to as a lacrimal plug or canalicular implant).

A punctum plug typically includes a retaining member which engages the edge of the punctum opening to retain the punctum plug in place within the punctum opening while supporting a distal section of the implant in the canaliculus adjacent to the punctum opening. The punctum plug functions to occlude the punctum opening and the retaining member is intended to prevent migration of the implant into the canaliculus, which is undesirable.

A lacrimal implant (or lacrimal plug or canalicular implant) typically does not include a retainer member but is formed of a dimension and shape to have the entire implant inserted into and through the punctum opening into the canaliculus. The lacrimal implant may be located in the canaliculus just beyond the punctum opening to function in the same manner as or to be equivalent to a punctum plug. Alternatively, the lacrimal implant could be positioned at any location within the canaliculus between the punctum opening and the nasal sac to occlude the canaliculus.

The term "implant" as used herein is intended to broadly cover any device, apparatus, element or structure which functions to partially or fully occlude the lacrimal system including any member, element, stent (metal or composition), any composition including chemical compositions, chemical compounds or chemical combinations which are adapted to be inserted into or through the punctum opening or into the canaliculus including all chemical compositions, chemical compounds or chemical combinations inserted into, placed into or injected into or implanted within the punctum opening or canaliculus in a first state; e.g., as a liquid, semi-liquid, soft or flexible material, gel or the like, and which changes into a second state or which is changed, controlled or uncontrolled, into a second state (e.g. by heat, infrared radiation, time, etc.) to perform to a partial or full occlusion, and including any implant used as an lacrimal blocking or control device, punctum plug, lacrimal plug, canalicular implant and any other type or equivalent type of lacrimal occluder.

The intended use for implants are for treatment of dry eye, or the dry eye component of ocular surface diseases. After surgery, an implant is used to: (i) prevent complications due to dry eye; (ii) enhance the efficacy of ocular medications; (iii) for treatment of dry eye related to contact lens problems; and (iv) as an adjunct aid in the treatment of other external eye diseases. In the preferred embodiment the lacrimal plugs, in the form of the implants as shown in FIGS. 21 through 30, and are fabricated from medical grade silicone.

In the present invention, the implant, as a generic structure, comprises an elongated member having a pair of spaced ends. One of the pair of ends includes a distal section that extends in a direction substantially parallel to the central axis. The distal section may include a distal tip to facilitate dilation of the punctum opening and/or enable the distal section to be inserted into, through and past the punctum opening. The other of the pair of end can be formed into a predetermined shape or structure to enable the implant to be used as either a punctum plug or as a lacrimal implant. The elongated member and the distal section are formed of a dimension to be inserted into and passed through a punctum opening of an eye.

If the implant is used as a punctum plug, then the distal section is inserted into and passed through the punctum opening and is transported into that portion of the canaliculus located between the punctum opening 44 and/or the ampula 54 that comprises a portion of either of the lower canaliculus 48 or the upper canaliculus 50.

If the implant is used as a lacrimal implant or lacrimal plug or canalicular implant, then the distal section and elongated body including the pair of ends are inserted into, through and past the punctum opening and is transported into a selected portion of the lower canaliculus 48 or the upper canaliculus 50.

It has developed that mechanism of lacrimal drainage results in the drainage of tear flow from the eye. One article which describes this phenomenon is entitled "*BLINKING AND THE MECHANICS OF THE LACRIMAL DRAINAGE SYSTEM*" by Marshall G. Doane, Ph.D., which appeared in OPHTHALMOLOGY, Volume 88, No. 8, August 1981, pages 844 through 851 inclusive (the "Doane Article"). The Doane Article describes that during each blink cycle, the upper lid sweeps down over the eye. As the lid descends, the papillae containing the punctal opening elevate from the medial lid margin. As the lid continues to descend, the puncta are occluded by the contact of the lid margins. Further lid closure squeezes the canaliculi and sac forcing the tear or contained fluid to drain into the nasolacrimal duct. At the end of a complete lid closure, the lacrimal system is compressed and largely empty of fluid. During the opening phase, the puncta are still occluded. The walls of the passageways or canaliculus expand by elastic force causing a partial vacuum or suction. As the lid continue to open, the puncta "pop" apart, and excess tear fluid is immediately drawn off the eye into the canaliculus.

The insertion of an implant into the canaliculus tends to retard the squeezing action of the canaliculi during eyelid closure and to reduce the partial vacuum during eyelid opening which results in a larger quantity of tear fluid remaining on the eye. If medication is added to the eye, it remains on the eye longer thereby effecting the eye treatment by the medication that, otherwise, would be removed by the blinking and the mechanics of the lacrimal drainage system.

The prior art Freeman punctum plug illustrated in FIG. 2(*a*) has a body 100, a barbed shaped distal end 102 and a rectangular top 104 and is adapted to be implanted in the punctum opening and in that portion of the canaliculus adjacent the punctum opening.

The prior art Freeman punctum plug illustrated in FIG. 2(*b*) having an elongated central member 110, a dome-shaped top 112 and a truncated distal tip 114 is adapted to be implanted in the punctum opening and in that portion of the canaliculus adjacent the punctum opening.

The prior art Herrick punctum plug illustrated in FIG. 3 has an elongated body 116 having a pair of spaced ends 118 and 120 and a collapsible expanded section 122 located between the ends 118 and 120. The end 118 terminates in a distal tip 124 which is substantially co-axial with the central axis of the elongated body 116 located within the canaliculus. The end 120 terminates in a thin retaining lip 136 which extends in an anterior direction and which is adapted to be oriented to extend beyond the edge of the punctum opening 140 and to engage the lip margin defining the eyelid implanted in the punctum opening and in that portion of the canaliculus adjacent the punctum opening 140.

FIG. 4 is a diagrammatic representation of a canaliculus shown generally as 144 which extends from the punctum opening 146, through that portion of the canaliculus 150 adjacent the punctum medial opening and into the ampula 154 and into that portion of the canaliculus 158 extending beyond the ampula 154 and the medial opening 160 thereof into and into the nasal sac shown generally as 162.

The table set forth below sets forth some typical dimensions of the lacrimal system illustrated and described in connection with FIG. 4.

DIMENSIONS OF ELEMENT OF A TYPICAL LACRIMAL SYSTEM

Table of Dimensions of Lacrimal Apparatus

| Element | Anatomical Name/Description | Typical Range |
|---|---|---|
| 146 | Punctum opening | .3 mm to .8 mm |
| 150 | Canaliculus extending form Punctum Opening | 2.0 mm to 2.5 mm |
| 154 | Ampula or horizontal sac of horizontal canaliculus | 1.0 mm to 3.0 mm |

Table of Demensions of Lacrimal Apparatus

| Element | Anatomical Name/Description | Typical Range |
|---|---|---|
| 158 | Reduced opening of horizontal canaliculus | .5 mm to .6 mm |
| 144 | Length of horizontal canaliculus | 7.5 mm to 8.5 mm |

In the pictorial representation of FIG. 5, an anterior lacrimal system 170 and posterior lacrimal system 144 communicate with opening 162 in the nasal sac 172. The relative size of the lacrimal system to the size of the nasal sac discloses that the nasal sac is larger. Of importance, however, is that the general a shape and configuration of the lacrimal system and the nasal sac, from an anatomical aspect, disclose that the structure thereof are quite similar.

In FIG. 6, the cross-section of a punctum plug 178, incorporating the teachings of this invention discloses that the punctum plug or implant comprises an elongated member 180 having central axis and a pair of spaced ends 184 and 186. One of the pair of ends, end 184, includes a distal section 188 that terminates in a distal tip 190 which extends in a direction substantially parallel to the central axis of the elongated member 180. The elongated member 180 and the distal tip 190 are formed of a dimension to pass through a punctum opening 146 and into the canaliculus 158 of an eye.

In FIG. 6, the distal section, forming one end 184 is illustrated, in the preferred embodiment, to be a collapsible expanded section and the other of the pair of ends 186 includes a thin retaining lip which in this preferred embodiment, is in the form of a thin elongated lip 194. The thin elongated lip 194 is positioned on the elongated member 180 such that the thin elongated tip 194 is positioned to extend in a generally anterior direction upon insertion of the same into a punctum opening 146.

In FIG. 6, the punctum plug 178 is illustrated as being implanted in the punctum opening 146 and in that portion of the canaliculus 150 adjacent the punctum opening with the elongated distal section 188 located in the ampula and the elongated distal tip 190 extending through the reduced opening 158 into the canaliculus 144.

FIG. 7 is a pictorial representation partially in cross-section of another embodiment of a punctum plug 200 incorporating the teachings of this invention where the collapsible extended section has a sloping outer edge 204 and terminates in elongated distal starting tip 190 which extends substantially parallel to the axis of the elongated body. Starting tip 190 is used, as an example, in the implants or FIG. 8 through FIG. 19 discussed below.

FIG. 8 is a front elevational view of yet another embodiment 206, which is similar to that illustrated in FIG. 7, wherein the elongated body is substantially straight.

FIG. 9 is a left side plan view of still yet another embodiment 208 similar to that illustrated in FIG. 8 wherein the elongated body is substantially straight and the outer edge 210 of the collapsible expanded section 212 is substantially planar.

FIG. 10 is a front elevational view of a punctum plug 216 similar to that illustrated in FIG. 8 wherein the outer edge 218 has a slight upward curve.

FIG. 11 is a left side plan view of a punctum plug 222 similar to that illustrated in FIG. 7 having a non-uniform shaped collapsible expanded section 224.

FIG. 12 is a front elevational view of a punctum plug 228 similar to that illustrated in FIG. 7 having a non-uniform shaped collapsible expanded section 230.

FIGS. 13 and 14 illustrate in a front elevational view and rotated view a punctum plug 232 having a collapsible expanded section in the form of a collapsible flared section 236 having a planar outer edge 238. The second end 242 is deflected at a slight angle to position the thin elongated lip 244 anterior to the cornea of an eye.

For purposes hereof, the term "thin elongated lip" means an extension or lip which extends or protrudes beyond the outer surface of the elongated member and which would be located around approximately 300° or less of the periphery of the elongated member leaving the posterior surface thereof free from protruding into, or from contacting with or from abrading the cornea or conjunctiva of an eye.

FIG. 14 clearly illustrated the relationship between the second end 242 and that the slight angle thereof supports the thin elongated lip 242 anterior of the cornea of an eye.

In FIG. 15, the cross-section of the elongated central member 250 and outer edge 254 of the collapsible flared section 252 are both circular.

In FIG. 16, the cross-section of the central member 260 and outer edge 264 of the collapsible flared section 262 are both oval.

In the front, top and left side perspective view of the punctum plug 232 illustrated in FIG. 17, which corresponds generally to the punctum plug 232 illustrated in FIGS. 13 and 14, the slight angle of the second end 242 positioned the thin elongated lip 242 anterior of the cornea of the eye. The distal tip 190 is substantially parallel or co-axial with the axis of the elongated body. When the punctum plug 232 is implanted, the distal tip 190 is oriented so to be located with the canaliculus urging and supporting the thin elongated lip 244 in a position to enable the same to engage and be supported by the edge of the punctum opening and the lip margin of an eyelid.

Figure 18:
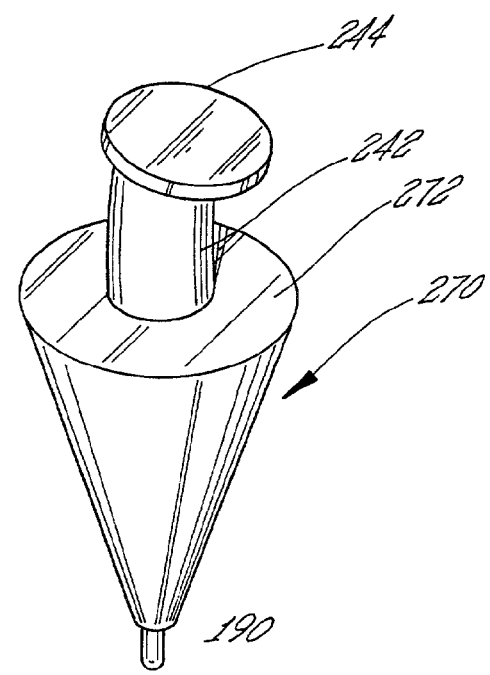
FIG. 18 is a front top and left side perspective view of the implant used as a punctum plug similar to that illustrated in FIG. 17 except that the collapsible expanded section is formed of a material which is compressible.

In FIG. 18, the front, top and left side perspective view of the punctum plug 270 is similar to that illustrated in FIG. 17 with respect to second end 242 and thin elongated lip 244 except that the collapsible expanded section 272 is formed of a material which is compressible. This results in a punctum plug that compresses upon insertion as opposed to being collapsed, as is the case for punctum plug 232 illustrated in FIG. 17. Upon passing and compressing of the collapsible expanded section 272 by the punctum opening, the compressed section then transitioning to an uncompressed section and goes back to its original state.

Figure 19:
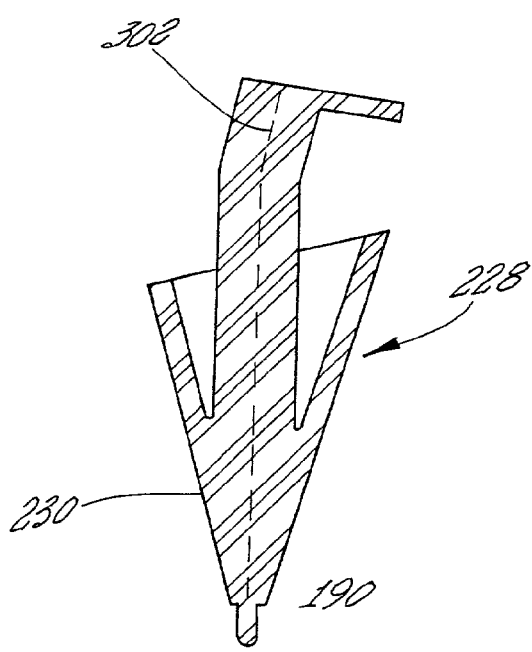
FIG. 19 is a cross-sectional view of the implant used as a punctum plug illustrated in FIG. 12.

FIG. 19 is a cross-sectional view of the punctum plug 228 with the distal tip 190 as illustrated in FIG. 12.

FIG. 20 is a pictorial representation of a punctum plug 284 using the teachings of the present having a central body 280 having first end 282 having an elongated distal tip 286 and a second end 284 having a thin elongated lip 288 wherein the elongated substantially perpendicular distal tip 286 is used as an anchor for a stent to repair canalicular lacerations and to block fluid flow through a canalicular canal. The stent defined by the elongated distal tip 286 passes into the opening 162 and the tip may just slightly extend into the nasal sac 172. If the stent 280 becomes separated from the central body 280, the stent having the energy blocking material incorporated therein can be located and removed.

In utilizing the punctum plug or implant for practicing the teaching of the invention, the eye surgeon can utilize any one of a number of methods for determining if an external condition due to a deficiency of tears exists. In the preferred embodiment of the present invention, the canaliculus can be temporarily occluded by placing a temporary implant (which may be a temporary punctum plug or canalicular implant) to provide a temporary blockage of the punctum opening or canaliculus as the case may be. By utilizing a temporary implant for providing temporary blockage, the eye surgeon can observe the response of the patient to the temporary blockade. If an improvement in the eye condition of the patient is noted, a permanent implant in the form of either a punctum plug or lacrimal implant can be implanted within the punctum opening or the canaliculus of the patient.

It is envisioned that the temporary implant used in practicing the invention can be in the form of one of the embodiments described hereinbefore. If an implant is to function as a temporary punctum plug or temporary lacrimal implant to provide temporary blockage of the punctum opening or of a portion of the canaliculus, the temporary implant can be fabricated from a medically grade, dissolvable biodegradable material such as collagen, catgut, biodegradable suturing material, polyglycolic acid or other medical compositions or material known to persons skilled in the art and approved for such use by the FDA. The temporary punctum plug or implant can be inserted into the punctum opening and any location within the canaliculus utilizing the procedures set forth hereinbelow.

If the eye surgeon determines that a permanent occlusion of the punctum opening or of the canaliculus is desirable, a permanent implant in the form of a punctum plug or lacrimal implant can be utilized as a means for providing a permanent occlusion of the selected punctum opening or selected portion of the canaliculus. In such event, the permanent punctum plug or implant can be fabricated from a medical grade non-biodegradable material or material and one which is not absorbable by or dissolved in the human body. Examples of such materials are medical grade rubber, silicone, polyethylene, polypropylene, polytetrafluoroethylene (e.g. Teflon) and other medical compositions or material known to persons skilled in the art and approved for such use by the FDA.

If an implant is used as a punctum plug, the diameter of the elongated member of the punctum plug would be in the order of about 0.2 mm to about 1.2 mm and the overall length could be in the order of about 2.5 mm to about 8 mm. The preferred diameter for elongated member of the punctum plug is in the order of about 0.5 mm to about 1.0 mm.

If an implant having a shape or structure disclosed in U.S. Pat. No. 5,049,142 is used as a lacrimal implant or lacrimal plug, the diameter of the elongated member of the lacrimal implant or lacrimal plug would be in the order of about 0.2 mm to about 1.2 mm and the overall length could be in the order of about 4 mm to about 8 mm. If a lacrimal implant, lacrimal plug or canalicular implant having a collapsible flared section as described in U.S. Pat. No. 5,163,959 is used as either a punctum plug or as a lacrimal implant or lacrimal plug, which is envisioned by this invention, the outer edge of the collapsible flared section would have a diameter in the order of about 0.5 mil to about 1.5 mm. The thickness of the thin-walled, conical shaped member would be about 700 mm.

Referring now to the pictorial representations of FIGS. 21(*a*) through 21(*e*).

FIGS. 21(*a*) through 21(*e*) illustrate the method for inserting an implant as a punctum plug illustrated in FIGS. 13, 14 and 17 into the punctum opening 146 and into that portion of the canaliculus extending from the punctum opening. In FIG. 21(*a*) the distal tip 190 is shown as an alternative embodiment having a length which is slightly longer than the length of distal tip 190 in FIG. 21(*b*).

In FIGS. 21(*a*) through 22(*e*), the pictorial representations are shown based upon the punctum plug 232 being inserted into the punctum opening 146, through that portion of the canaliculus shown as 150 and into the canaliculus 144.

In connection with the punctum plug 232 illustrated in FIGS. 21(*a*) through 21(*e*), the length of the punctum plug 232 and the length of the elongated distal tip 190 can be selected to place the collapsible flared section 236 into the lower canaliculus 48 of FIG. 1.

Of course, the punctum plug 232 could be inserted into the upper canaliculus 50 in a similar manner as that described below.

As illustrated in FIG. 21(*b*), the elongated distal tip 190 is positioned adjacent the distal starting tip 290 in a position to penetrate the punctum opening 146 such that the distal tip 190 will gently expand the fibrous ring defining the punctum opening 146 to pass the distal section of the implant as the implant is passed through the punctum opening 146 and is directed towards the lower canaliculus 48. The step of urging the elongated distal tip 190 into and through the punctum opening 146 can include using an insertion tool, illustrated by dashed line 300 in FIG. 21(*b*), which is inserted into the second end to apply force to urge the punctum plug through the punctum opening and into the that portion of the canaliculus communicating with or adjacent the punctum opening.

In FIG. 21(*c*), the punctum plug 232 is rotated as required to urge the collapsible flared section 236 through the punctum opening 146 until the punctum opening 146 engages the exterior surface of the collapsible flared section 236.

FIG. 21(*c*) illustrates that the punctum opening 146 slideably engages the collapsible flared section 236 as an insertion force is applied to the punctum plug 232. A radial force is developed around the surface of the collapsible flared section 236 as the punctum plug 30 slideably moves past the punctum opening 146. A radial force is applied to the collapsible flared section 236 in a direction so as to cause the collapsible flared section to be urged into its collapsed position. A clamping force is developed between the outer walls of the collapsed conical-shaped member defining the collapsible flared section 236 and the inner walls of section 150 of the canaliculus.

In FIG. 21(*d*), the collapsible expanded section 236 is illustrated as entering into the ampula 154 orienting the distal tip 190 towards the reduced opening 158.

FIG. 21(*e*), illustrates the fully inserted implant 232 has the collapsible expanded section 236 expanded back into the original shape and the expanded section 236 is positioned with the ampula 154 and the portion 150 of the canaliculus is occluded. The elongated distal tip 190 extends into the reduced opening 158 to position the thin elongated lip 242 in contact with and against the margin of the eye.

In FIG. 22, the implant 300 is in the form of a canalicular implant having a central body 302, a distal section 306 terminating in a distal tip 332, and a proximal end 334 terminating in a collapsible flared section 336. Collapsible flared section 336 defines a central opening 342 in the center of the collapsible flared section 336 which is adapted to cooperate with an insertion tool at the opening 346.

In FIG. 23, the embodiment of a canalicular implant 352 is a variation of the canalicular implant of FIG. 22 except that implant 352 has an elongated central opening 358, which is longer along its central axis and is adapted to cooperate with an insertion tool.

FIG. 24 is an alternate embodiment of a canalicular implant 400 which is a variation of the canalicular implant of FIG. 22 having a collapsible flared section 402 having a "V" shaped central section 404 which is adapted to cooperate with an insertion tool. In the implants of FIGS. 22, 23 and 24, the energy wave blocking material or radiation blocking material pigment elements are disseminated in part of or all of the implant.

The canalicular implant of 412 of FIG. 25 is of the same shape as implant 400 of FIG. 24 without the pigment elements forming the energy blocking material being disseminated therethrough. The radiation blocking material shown as layer on coating 414 is coated thereon in lieu of the pigment elements forming the energy blocking material being disseminated within part of or all of the implants.

Thus, the energy blocking material can be incorporated into the implant in a number of ways, e.g., dissemination, located, laminated or other techniques known in the art.

FIG. 26, illustrates as a pictorial illustration a lower canaliculus 490 having a punctum opening 470 which is defined by a punctum sphincter 476, a canaliculus 478 defined by a canaliculus wall 496. The implant 300 illustrated in FIG. 22 is pictorial illustrated as being inserted in and located within the canaliculus 478.

Although the implant 300 of FIG. 22 is illustrated in FIG. 26, the implant 350 of FIG. 23. This implant 400 of FIG. 24 and the implant 412 of FIG. 25 should likewise be inserted into the canaliculus 478 in the same manner as implant 300 illustrated in FIG. 26.

FIG. 27, illustrates as a pictorial representation the relationship between the canaliculus wall 496 and the implant 300. As illustrated in FIG. 27, the collapsible flared section 336 has been compressed or collapsible by the canaliculus wall 496 and the clamping action therebetween is relied upon to prevent the implant 300 from migrating within the canaliculus 478. The implant 300 is transported to the desired location within the canaliculus 478 by means of an insertion tool or other insertion means known to persons skilled in the art, such as, for example, an insertion wire, all of which is depicted by arrow 442. The implant 300 can be modified to provide for a lacrimal drainage channel depicted by dash lines 494 to allow a controlled or metered portion of the tear flow to pass through the collapsible flared section 336, the elongated opening 346 and through the lacrimal drainage channel 494 where the canaliculus 478 would then carry the tear or fluid flow into the nasal sac.

Figure 28:
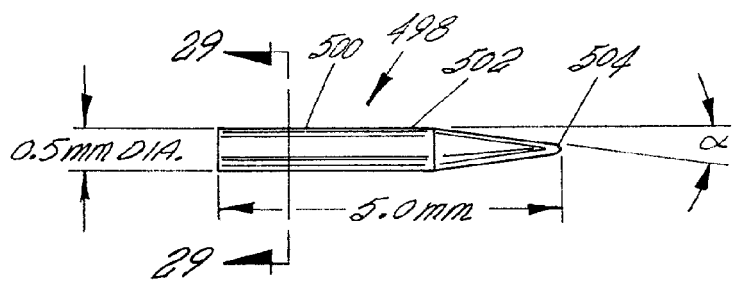
FIG. 28 is front elevational view of an implant using the teachings of this invention having an elongated member having a pair of spaced ends wherein one of said pair of ends includes a distal section which extends in a direction substantially parallel to the central axis being formed of a dimension to be inserted into and passed through a punctum opening of an eye.

FIG. 28, illustrates a lacrimal implant or lacrimal plug 498 comprising another embodiment of an implant having an elongated central body 502, a first end or proximal end 500 in the form of a cylindrically shaped end and a second or distal end section 504 in the form of tapered distal tip having a slope shown as angle alpha wherein an energy blocking material is incorporated into the implant.

Figures 29, 30, 31:
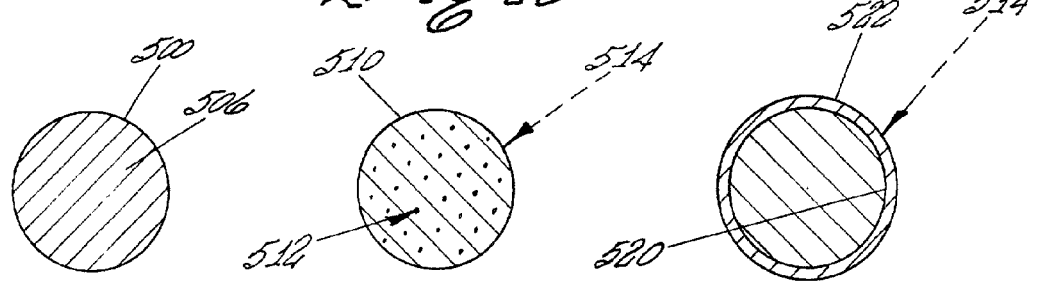
FIG. 29 is a cross-sectional view taken along section lines 29-29 of FIG. 28.
FIG. 30 is a pictorial representation of a cross-section of an elongated member showing an energy obstructing material responsive to the application of an energy wave being disseminated into or integral with the elongated member.
FIG. 31 is a pictorial representation of a cross-section of an implant having an energy obstructing material responsive to the application of an energy wave coated thereon.

FIG. 29, when taken along sections line 29-29 of FIG. 30, shows the proximal end 500 and that the central body has a composition 506 having pigment elements 512 dissemination therethrough.

In FIG. 30, the pictorial representation of the cross-section of an elongated member 502 shows that the implant 510 has an energy obstructing material responsive to the application of an energy wave disseminated within the composition of the elongated member as depicted by pigment elements 512. An energy wave depicted by arrow 514 is selectively blocked by the pigment element.

FIG. 31, the pictorial representation of a cross-section of a distal section similar to that of FIG. 28, shows that the implant 498 has a layer 522 energy obstructing material responsive to the application of an energy wave 514 coated on the outer surface 520 of the entire implant 498 including central body 502. The layer of coated material would preferably have a thickness of about at least 0.0001 inch to about 0.0010 inch. In the preferred embodiment, an opaque material, such as pigment e.g. 5% titanium dioxide could be coated thereon which is responsive to a visible light radiation from a simple light source such as an incandescent bulb. The energy obstructing material would be selected to be operative with an appropriate energy source, e.g. a source of electromagnetic radiation at a selected wavelength.

By using the implant capable of forming a differential image in an eye of the present invention, a non-invasive visual verification can be performed to determine the location of the implant. In FIG. 26, the pictorial representation illustrates an eye having a lacrimal implant comprising an elongated member having a pair of spaced ends wherein one of the pair of ends includes a distal section which extends in a direction substantially parallel to the central axis. The elongated member and the distal section are formed of a dimension enabling the implant to be inserted into and passed through a punctum opening of an eye into the canaliculus. The implant includes an energy obstructing material responsive to the application of an energy wave that has been incorporated into at least one of the elongated member and the distal section. In this example, the energy obstructing material is selected to be a pigment comprising about 3% to about 10% titanium dioxide which is responsive to radiation in the visible light wavelength with about 5% titanium dioxide being preferred.

Figure 32:
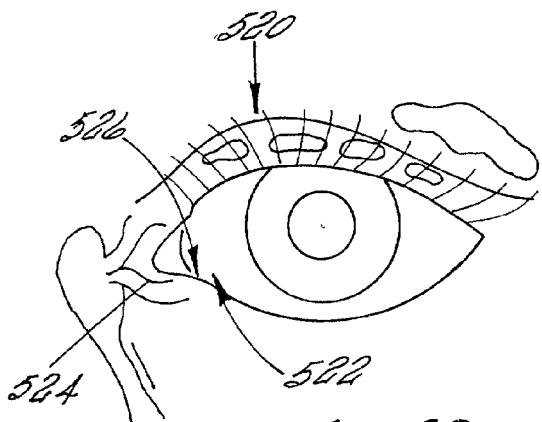
FIG. 32 is a pictorial representation of an eye having an implant having a radiation obstructing material positioned within the canaliculus which is to be located using the teaching of the present invention.

FIG. 32 illustrates an eye 520 having a punctum opening 522 having an implant located in the canaliculus 524. The eyelid can be everted, e.g., turned away from the eye by application of a force as shown by arrow 526.

Figure 33:
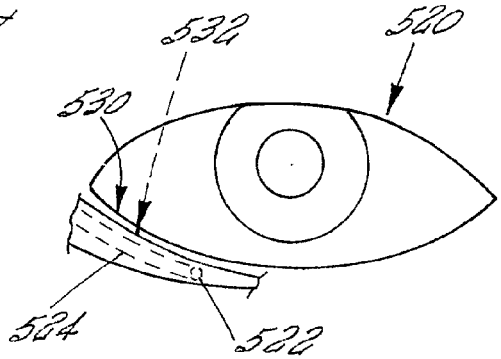
FIG. 33 is a pictorial representation of an everted eye lid exposing the implant having a radiation obstructing material to an energy wave.

In FIG. 33, the eyelid 530 has been inverted by force 526 exposing the canaliculus 524 having the implant located therein to radiation in the visible light wavelength illustrated by arrow 532. This procedure is generally referred to as transillumination of the lid and is used to visualize the exact location of the plug within the canaliculus including punctum plugs which have migrated into the canaliculus. Transillumination can be used to confirm the presence of an implant anytime after insertion and the absence of an implant after a removal procedure.

Figure 34:
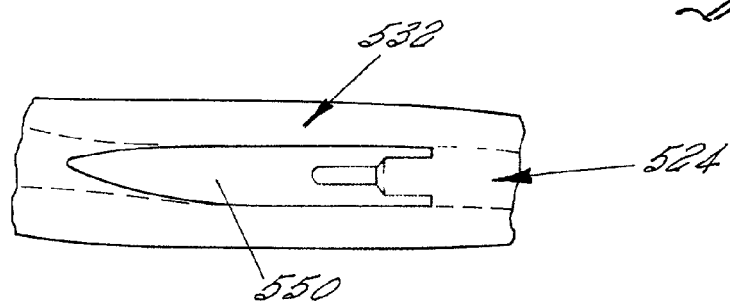
FIG. 34 is a pictorial representation of a differential image pattern formed by an implant having an energy obstructing material being responsive to the application of an energy wave showing the location of the implant in the eye.

The pictorial representation of FIG. 34 illustrates the differential image pattern formed by the implant 550 having the energy obstructing material which is responsive to the application of the selected energy wave to show the location of implant 550 in the eye canaliculus 524 in the eye.

By utilizing the teachings of the present invention, a method for treating external eye conditions due to a deficiency of tears is disclosed. The method includes the steps of testing the eye to determine if a tear deficiency exists; and, if a tear deficiency is determined, inserting into the punctum opening an implant capable of forming a differential image in an eye comprising an elongated member having a pair of spaced ends wherein one of the pair of ends includes a distal section which extends in a direction substantially parallel to the central axis and wherein the elongated member and the distal section are formed of a dimension to be inserted into and passed through a punctum opening of an eye and wherein the implant has incorporated therein, in at least one of the elongated member and the distal section and preferably in the entire implant, an energy obstructing material responsive to the application of an energy wave which upon everting of an eyelid of an eye and exposing the implant to an energy wave forms a differential image pattern showing the location of the implant in the eye.

The present invention also teaches a method for locating an implant in the canaliculus of an eye comprising the step of incorporating in an implant an energy obstructing material responsive to the application of an energy wave capable of forming a differential image in an eye wherein the implant comprising an elongated member having a pair of spaced ends wherein one of the pair of ends includes a distal section which extends in a direction substantially parallel to the central axis, the elongated member and the distal section being formed of a dimension to be inserted into and passed through a punctum opening of an eye; everting an eyelid of an eye; and exposing the implant to an energy wave to form a differential image pattern showing the location of said implant in the eye.

The punctum plug or implant of the present invention utilizes the collapsible flared section for occluding the punctum opening and the canaliculus, and the punctum plug is held in place by the thin elongated tip at the second end being urged against the margin of the eye and the elongated distal tip which extends into the reduced opening of the horizontal canaliculus. By selecting a punctum plug of an appropriate length, the above elements are effective to hold the plug in place and to prevent inadvertent removal or any possible migration of the plug while implanted within the eye.

The punctum plug of the present invention is preferably used as a permanent implant for practicing the invention. In the method disclosed and taught herein, the temporary implant could be an implant well known in the art, could be a means for occluding the punctum opening and the canaliculus, could be a temporary implant as disclosed in the prior art section above or any other means known in the art for temporarily occluding the eye to determine if an improvement in eye condition is noted.

However, the temporary implant could, likewise, be a punctum plug or implant having a structure disclosed herein wherein the implant is formed of an absorbable or dissolvable (in the body) biodegradable material. The permanent punctum plug or implant can be identical in shape, size and dimension but be formed of a non-biodegradable, non-absorbable or non-dissolvable (in the body) material. The advantage of utilizing a temporary implant and a permanent implant having a structure as disclosed herein is that the collapsible flared section of the canalicular implant performs the function of occluding the punctum opening and/or the canaliculus. If the punctum plug does not extend all the way into the canaliculus and remains within the punctum opening and the that portion of the canaliculus which communicates with the punctum opening, the collapsible flared section develops a clamping pressure between the collapsible flared section and the interior walls of the punctum opening or the canaliculus while providing the desired blockage to the eye.

If it is desirable to have a small passageway available to enable a limited flow of tears to pass through the occlusion, it is envisioned that the punctum plug or implant could have an aperture extending axially through the center thereof. For example, the punctum plug could have a lacrimal fluid control opening, such as shown by dashed line opening 494 in FIG. 27, to provide a passageway of a predetermined diameter to control tear secretion flow or, the alternative, a slot could be formed around the periphery thereof to facilitate a partial tear flow.

Typical dimensions for the punctum plug may include the elongated member having a diameter of about 0.5 mm to about 1.2 mm. The diameter of the outer ring defining the outer edge of the collapsible flared section may be in the order of about 1.5 mm to about 2.5 mm. The overall length of the implant could be about 2.5 mm to about 8 mm.

The diameter of the distal starting tip can be about 0.2 mm to about 0.4 mm with about 0.3 mm being preferred.

The length of the elongated distal tip could be in the range of about 1.5 mm to about 3.0 mm The preferred embodiments and the various shapes, sizes and design for the punctum plug or implants disclosed herein are exemplary, and all variations thereof are contemplated to be within the teaching of and scope of this invention.

What is claimed is:

1. An implant capable of forming a differential image in an eye comprising:

an elongated member having a central axis and a pair of spaced ends wherein one of said pair of ends includes a distal section which extends in a direction substantially parallel to the central axis, said elongated member and said distal section being formed of a dimension to be inserted into and passed through a punctum opening of an eye; and a radiation obstructing material responsive to electromagnetic radiation being incorporated in at least one of said elongated member and said distal section which, in use, upon everting of an eyelid of an eye and exposing the implant to electromagnetic radiation at a selected wavelength forms a differential image pattern showing the location of said implant in the eye wherein said radiation obstructing material is responsive to electromagnetic radiation at said selected wavelength and wherein said radiation obstructing material comprises a pigment comprising about 3% to about 10% titanium dioxide.

2. The implant of claim 1 wherein said a radiation obstructing material is integral with at least one of said elongated member and said distal section.

3. The implant of claim 1 wherein said radiation obstructing material is coated on at least one of said elongated member and said distal section.

4. The implant of claim 1 wherein said a radiation obstructing material is integral with the implant.

5. The implant of claim 1 wherein said radiation obstructing material is coated on the implant.

6. The implant of claim 1 wherein said radiation obstructing material responsive to electromagnetic radiation at a selected wavelength in the visible light range is incorporated in at least one of said elongated member and said distal section which, in use, upon everting of an eyelid of an eye and exposing the implant to electromagnetic radiation at said selected wavelength forms a differential image pattern showing the location of said implant in the eye.

7. An implant capable of forming a differential image in an eye comprising:

an elongated member having a central axis a pair of spaced ends wherein one of said pair of ends includes a distal section which extends in a direction substantially parallel to the central axis, said elongated member and said distal section being formed of a dimension to be inserted into and passed through a punctum opening of an eye; and a substantially opaque material responsive to electromagnetic radiation in the wavelength of visible light incorporated in at least one of said elongated member and distal section which, in use, upon everting of an eyelid of an eye and exposing the implant to electromagnetic radiation in the wavelength of visible light forms a differential image pattern showing the location of said implant in the eye and wherein said opaque material comprises a pigment comprising about 3% to about 10% titanium dioxide.

8. The implant of claim 7 wherein said distal section terminates in a distal tip.

9. The implant of claim 7 wherein said distal section terminates in a distal tip having a collapsible expanded section.

10. The implant of claim 9 wherein said collapsible expanded section is in the form of a collapsible flared section.

11. The implant of claim 7 wherein said distal section terminates in a distal tip having a collapsible expanded section and the other of said pair of ends includes a proximal section, said proximal section being positioned on the elongated member to position the implant at a selected location in the canaliculus beyond the punctum opening.

12. The implant of claim 7 wherein said distal section terminates in a distal tip having a collapsible expanded section and the other of said pair of ends includes a proximal section, said proximal section being located on the elongated member to enable positioning of the implant at a selected location in the canaliculus between the punctum opening and nasal sac including the ampula.

13. The implant of claim 7 wherein said distal section terminates in a distal tip having a collapsible expanded section and the other of said pair of ends includes a proximal section, said proximal section being located on the elongated member to enable positioning of the implant at a selected location in the canaliculus between the punctum opening and ampula.

14. The implant of claim 7 wherein said distal section terminates in a distal tip having a collapsible expanded section and the other of said pair of ends includes a proximal section, said proximal section being located on the elongated member to enable positioning of the implant at a selected location in the canaliculus between the ampula and nasal sac.

15. The implant of claim 1 wherein said distal section terminates in a distal tip having a collapsible expanded section and the other of said pair of ends includes a thin retaining lip, said thin retaining lip being positioned on the elongated member configured to pass the distal tip through the punctum opening and to position the distal tip adjacent to the punctum opening whereupon the thin retaining lip engages a lip margin of an eyelid to occlude the punctum opening.

16. The implant of claim 6 wherein collapsible expanded section is in the form of a collapsible flared section and said thin retaining lip is in the form of a thin elongated lip extending in a generally anterior direction such that upon insertion of the collapsible flared section into and through a punctum opening positioning the thin elongated lip anterior of the cornea of an eye, the thin elongated lip is urged against the edge of the punctum opening and lid margin of an eyelid and occludes the punctum opening.

17. The implant of claim 16 wherein said thin elongated lip is capable of being positioned slightly anterior to the cornea of an eye whereupon the thin elongated lip is urged against the edge of the punctum opening and lid margin of an eyelid and occludes the punctum opening.

18. A locatable implant comprising
an elongated member having a central axis and a pair of spaced ends wherein one of said pair of ends includes a distal section terminating in a distal tip which extends in a direction substantially parallel to the central axis, said elongated member and said distal tip being formed of a dimension to be inserted into and passed through a punctum opening of an eye; and
a substantially opaque material responsive to electromagnetic radiation in the wavelength of visible light incorporated in at least one of said elongated member and distal tip which, in use, upon everting of an eyelid of an eye and exposing the implant to electromagnetic radiation in the wavelength of visible light forms a differential image pattern showing the location of said implant in the eye and wherein said opaque material comprises a pigment comprising about 3% to about 10% titanium dioxide.

19. The implement of claim 18 wherein said one of said pair of ends includes a collapsible expanded section and the other of said pair of ends includes a thin retaining lip, said thin elongated lip being positioned on the elongated member to position the elongated tip to extend generally anterior direction upon insertion into a punctum opening.

20. The implant of claim 19 wherein the elongated member curves slightly in a direction towards said other of said pair of ends.

21. The implant of claim 19 wherein said collapsible expanded section is a collapsible flared section which is collapsible relative to said central axis in response to the application of a force on the collapsible flared section in a direction to collapse the same and urge the collapsible flared section into a collapsed position.

22. The implant of claim 21 wherein said collapsible expanded section has a substantially uniform shape for enabling said collapsible flared section to be uniformly collapsed relative to said central axis.

23. The implant of claim 21 wherein said collapsible expanded section is a collapsible flared section having a hollowed out central area defining a thin-walled, conical shaped member.

24. The implant of claim 23 wherein said collapsible flared section defines a substantially uniform shape for enabling said collapsible flared section to be uniformly collapsed relative to said central axis.

25. The implant of claim 23 wherein said collapsible flared section defines an outer edge that is located between said pair of ends.

26. The implant of claim 23 wherein said collapsible flared section has a substantially circular shaped outer edge which is located adjacent said one of said pair of ends.

27. The implant of claim 23 wherein said collapsible expanded section has a non-uniform shape for enabling said collapsed expanded section to be collapsed relative to said central axis.

28. The implant of claim 23 having a fluid control opening extending therethrough to pass lacrimal fluid.

29. The implant of claim 18 wherein the diameter of the distal tip is about 0.2 mm to about 0.4 mm.

30. The implant of claim 29 wherein the diameter of the distal tip is about 0.3 mm.

31. The implant of claim 18 wherein the implant is formed of a biodegradable material.

32. The implant of claim 31 wherein the biodegradable material is a collagen material.

33. The implant of claim 18 wherein the implant is formed of a non-biodegradable material.

34. The implant of claim 33 wherein the non-biodegradable material is a silicone material.

35. An implant adapted to be inserted into a punctum opening of an eye and be transported therethrough into and to occlude the canaliculus, said implant comprising
an elongated member having a central axis a first end and a spaced, opposed second end and a central member having a predetermined cross-sectional dimension extending from said first end to said second end;

said second end having a collapsible expanded section which varies in cross-section as the collapsible expanded section approaches the second end and which terminates in an outer edge having a dimension which is greater than the predetermined cross-sectional dimension of the central member, said collapsible expanded section having an extended distal section which extends in a direction substantially normal to the central axis, said collapsible expanded section having a geometrical dimension approximately equal to that of the punctum opening of an eye adapted to pass the same, and wherein the application of a radial force in a direction to collapse the collapsible expanded section urges the same from an extended position into a collapsed position; and a substantially opaque material responsive to electromagnetic radiation in the wavelength of visible light incorporated in at least one of said elongated member and distal section which, in use, upon everting of an eyelid of an eye and exposing the implant to electromagnetic radiation in the wavelength of visible light forms a differential image pattern showing the location of said implant in the eye and wherein said opaque material comprises a pigment comprising about 3% to about 10% titanium dioxide.

36. The implant of claim 35 wherein said first end includes a thin retaining lip having a section which extends in an anterior direction upon insertion and is adapted to engage a lip margin of an eye.

37. The implant of claim 36 wherein the elongated member has a slightly angular curve in a selected direction causing the first end to be slightly deflected relative to the second end for orienting and urging the section which extends in an anterior direction into holding engagement with the edge of a punctum opening and lip margin.

* * * * *